US012702723B2

(12) United States Patent
Childress et al.

(10) Patent No.: US 12,702,723 B2
(45) Date of Patent: Aug. 11, 2026

(54) ULTRAVIOLET LIGHT SANITIZING SYSTEMS AND METHODS

(71) Applicant: THE BOEING COMPANY, Chicago, IL (US)

(72) Inventors: Jamie J. Childress, Mercer Island, WA (US); Kevin S. Callahan, Everett, WA (US); Teresa A. King, Bothell, WA (US)

(73) Assignee: The Boeing Company, Arlington, VA (US)

(*) Notice: Subject to any disclaimer, the term of this patent is extended or adjusted under 35 U.S.C. 154(b) by 1314 days.

(21) Appl. No.: 17/348,889

(22) Filed: Jun. 16, 2021

(65) Prior Publication Data

US 2022/0111087 A1 Apr. 14, 2022

Related U.S. Application Data

(60) Provisional application No. 63/118,031, filed on Nov. 25, 2020, provisional application No. 63/091,444, filed on Oct. 14, 2020.

(51) Int. Cl.

| | |
|---|---|
| ***A61L 2/10*** | (2026.01) |
| ***A61L 2/24*** | (2006.01) |
| ***B64F 5/30*** | (2017.01) |
| *A61L 103/75* | (2026.01) |

(52) U.S. Cl.

CPC .................. *A61L 2/10* (2013.01); *A61L 2/24* (2013.01); *B64F 5/30* (2017.01); *A61L 2103/75* (2026.01); *A61L 2202/11* (2013.01); *A61L 2202/14* (2013.01)

(58) Field of Classification Search

None

See application file for complete search history.

(56) References Cited

U.S. PATENT DOCUMENTS

| | | | | |
|---|---|---|---|---|
| 2016/0136313 | A1* | 5/2016 | Nguyen | A61L 2/26<br>315/76 |
| 2018/0214592 | A1* | 8/2018 | Garner | A61L 2/10 |
| 2018/0369435 | A1* | 12/2018 | Dhiman | G01J 1/0228 |
| 2019/0070326 | A1* | 3/2019 | Xie | A61L 2/26 |
| 2021/0299868 | A1* | 9/2021 | Vitzrabin | A61L 2/24 |
| 2021/0387729 | A1* | 12/2021 | Subramanian | B64D 11/0606 |

(Continued)

FOREIGN PATENT DOCUMENTS

| | | |
|---|---|---|
| JP | 2018525063 | 9/2018 |
| KR | 200360140 | 8/2004 |

(Continued)

OTHER PUBLICATIONS

Detector Definition & Meaning, Merriam-Webster Dictionary, https://www.merriam-webster.com/dictionary/detector (Jan. 20, 2026).*

(Continued)

*Primary Examiner* — Holly Kipouros

(74) *Attorney, Agent, or Firm* — Joseph M. Butscher; Carroll, Hoette & Butscher, LLC

(57) ABSTRACT

A system and method for disinfecting one or more components include one or more ultraviolet (UV) lamps. The one or more UV lamps include one or more UV light emitters configured to emit UV light, and a mounting interface removably securable to a securing mount.

34 Claims, 28 Drawing Sheets

(56) References Cited

U.S. PATENT DOCUMENTS

| | | | | |
|---|---|---|---|---|
| 2022/0016437 | A1* | 1/2022 | Jarausch | A61L 2/24 |
| 2022/0031897 | A1* | 2/2022 | Saxena | B64F 5/30 |
| 2022/0090777 | A1* | 3/2022 | Edquist | A61L 2/08 |
| 2023/0270907 | A1* | 8/2023 | Klettke | A61L 2/26 |
| | | | | 422/24 |

FOREIGN PATENT DOCUMENTS

| | | |
|---|---|---|
| KR | 200463618 | 11/2012 |
| WO | WO 2019/178639 | 9/2019 |
| WO | WO 2019/190967 | 10/2019 |

OTHER PUBLICATIONS

Detects Definition & Meaning, Merriam-Webster Dictionary, https://www.merriam-webster.com/dictionary/detects (Jan. 20, 2026).*

Extended European Search Report for EP 21209988.1.1012, dated Apr. 19, 2022.

U.S. Appl. No. 17/016,466, filed Sep. 10, 2020.

U.S. Appl. No. 29/735,235, filed May 19, 2020.

U.S. Appl. No. 17/039,011, filed Sep. 30, 2020.

U.S. Appl. No. 17/026,414, filed Sep. 21, 2020.

U.S. Appl. No. 17/020,942, filed Sep. 15, 2020.

U.S. Appl. No. 16/987,514, filed Aug. 7, 2020.

U.S. Appl. No. 17/104,628, filed Nov. 25, 2020.

U.S. Appl. No. 16/987,647, filed Aug. 7, 2020.

U.S. Appl. No. 17/026,417, filed Sep. 21, 2020.

U.S. Appl. No. 17/020,951, filed Sep. 15, 2020.

"Honeywell UV Treatment System," https://aerospace.honeywell.com/en/learn/products/cabin/uv-cabin-system.

U.S. Appl. No. 17/026,435, filed Sep. 21, 2020.

U.S. Appl. No. 17/022,392, filed Sep. 16, 2020.

Communication re EP 21209988.1.1012, dated May 15, 2024.

Machine translation of KR 200360140.

* cited by examiner

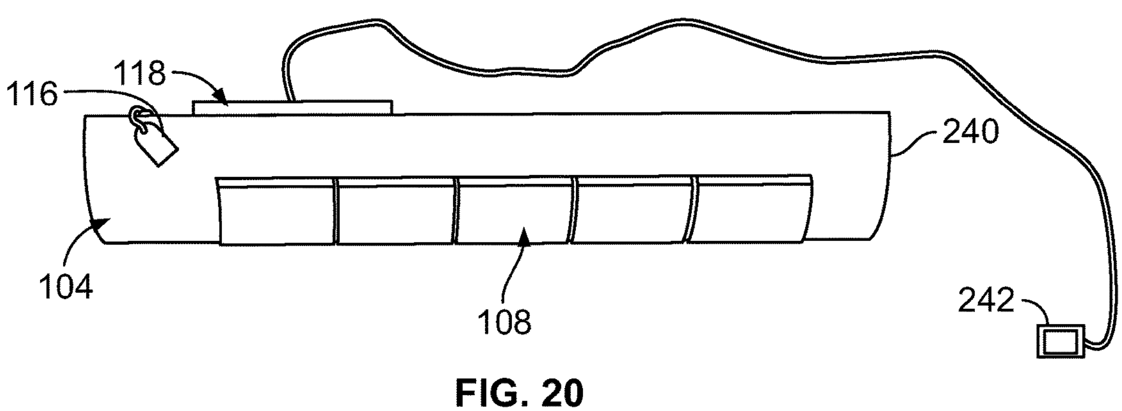
FIG. 20
FIG. 21
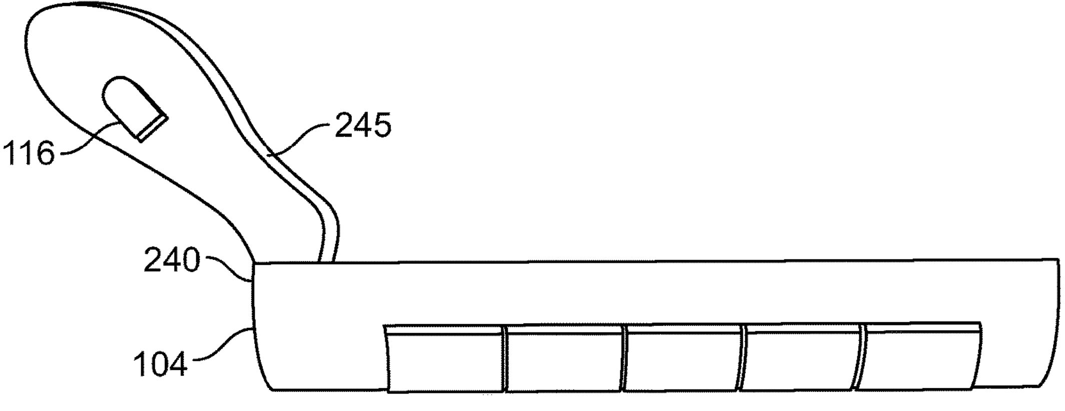
FIG. 22

402
404
446
442
444
440
400
106

ULTRAVIOLET LIGHT SANITIZING SYSTEMS AND METHODS

RELATED APPLICATIONS

This application relates to U.S. Provisional Patent Application No. 63/118,031, entitled "Ultraviolet Light Sanitizing Systems and Methods," filed Nov. 25, 2020, which is hereby incorporated by reference in its entirety.

This application also relates to U.S. Provisional Patent Application No. 63/091,444, entitled "Ultraviolet Light Sanitizing Systems and Methods," filed Oct. 14, 2020, which is hereby incorporated by reference in its entirety.

FIELD OF THE DISCLOSURE

Embodiments of the present disclosure generally relate to sanitizing systems, such as may be used to sanitize structures and areas within vehicles, and more particularly to systems and methods that sanitize components with ultraviolet (UV) light.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

A UV light sanitizing system typically includes a UV lamp that includes a plurality of UV light emitters. The UV lamp is formed by integrating the various UV light emitters into a single housing and coupling the UV light emitters to a separate power supply.

As can be appreciated, the UV lamp can have numerous UV light emitters. The process of manufacturing such a UV lamp is time and labor intensive. Further, if one or more of the UV light emitters malfunctions, replacing such may also prove time and labor intensive.

Further, in various settings, UV light disinfection occurs when an area is unoccupied. For example, a lavatory within an aircraft can be disinfected with UV light. However, such disinfection typically does not occur when an individual is within the lavatory.

Additionally, during operation, UV light emitters can generate electromagnetic interference (EMI), which can affect operation of the UV lamp and/or other devices.

Also, only certain areas within internal cabins may have a permanently installed UV disinfection system. For example, lavatories may include UV disinfection systems. However, various other areas of internal cabins may not include UV disinfection systems.

SUMMARY OF THE DISCLOSURE

A need exists for UV disinfection systems that can be easily mounted and secured throughout an area, such as internal cabin of an aircraft.

With that need in mind, certain embodiments of the present disclosure provide a system for disinfecting one or more components. The system includes one or more ultraviolet (UV) lamps. The one or more UV lamps include one or more UV light emitters configured to emit UV light, and a mounting interface removably securable to a securing mount.

In at least one embodiment, a control unit is configured to control operation of the one or more UV light emitters. For example, the one or more UV lamps can include the control unit.

In at least one embodiment, the one or more UV lamps include one or more sensors in communication with the control unit. The one or more sensors are configured to detect presence or movement proximate to the one or more UV lamps. Further, the control unit can be configured to control one or more a power level, an irradiance level, an intensity level, or a timing period for disinfection of the one or more UV lamps based on presence signals received from the one or more sensors. As an example, the control unit is configured to predict future operation of the one or more UV light emitters based on presence data stored in a memory.

In at least one embodiment, the one or more UV lamps include a position detector in communication with the control unit. The position detector is configured to detect a location of the one or more UV lamps within an area. As a further example, the control unit is configured to operate the one or more UV light emitters based on the location of the UV lamp, as detected by the position detector, within the area.

In at least one example, the one or more UV light emitters include first UV light emitters configured to emit the UV light at a first wavelength, and second UV light emitters configured to emit the UV light at a second wavelength that differs from the first wavelength. In at least one embodiment, the control unit is configured to control the one or more UV light emitters to emit the UV light at different wavelengths based on sensed or predicted behavior proximate to the UV lamp.

As an example, the one or more UV lamps include a power supply, and one or more batteries.

In at least one embodiment, the control unit is configured to operate the one or more UV light emitters based on a sensed output voltage.

In at least one embodiment, the one or more UV lamps include a plurality of UV lamps. The plurality of UV lamps are configured to communicate with each other.

In at least one embodiment, an external monitoring system is in communication with the one or more UV lamps. The external monitoring system is configured to control the one or more UV lamps.

Certain embodiments of the present disclosure provide a method for disinfecting one or more components. The method includes removably securing one or more ultraviolet (UV) lamps to a securing mount, wherein the one or more UV lamps includes one or more UV light emitters configured to emit UV light to a securing mount. In at least one embodiment, the method also includes controlling, by a control unit, operation of the one or more UV light emitters.

Certain embodiments of the present disclosure provide a system for disinfecting one or more components. The system includes a first subset of one or more ultraviolet (UV) lamps secured within a first area, a second subset of one or more UV lamps secured within a second area that is spaced apart from the first area, and a control unit. Each UV lamp in the first subset and the second subset includes one or more UV light emitters configured to emit UV light, and a mounting interface removably securable to a respective securing mount. The control unit is configured to control operation of the one or more UV light emitters in each of the UV lamps in the first subset and the second sub set.

BRIEF DESCRIPTION OF THE DRAWINGS

FIG. 20 illustrates a perspective bottom view of a UV lamp, according to an embodiment of the present disclosure.

FIG. 21 illustrates a perspective bottom view of a UV lamp, according to an embodiment of the present disclosure.

FIG. 22 illustrates a perspective bottom view of a UV lamp, according to an embodiment of the present disclosure.

DETAILED DESCRIPTION OF THE DISCLOSURE

Figure 1:
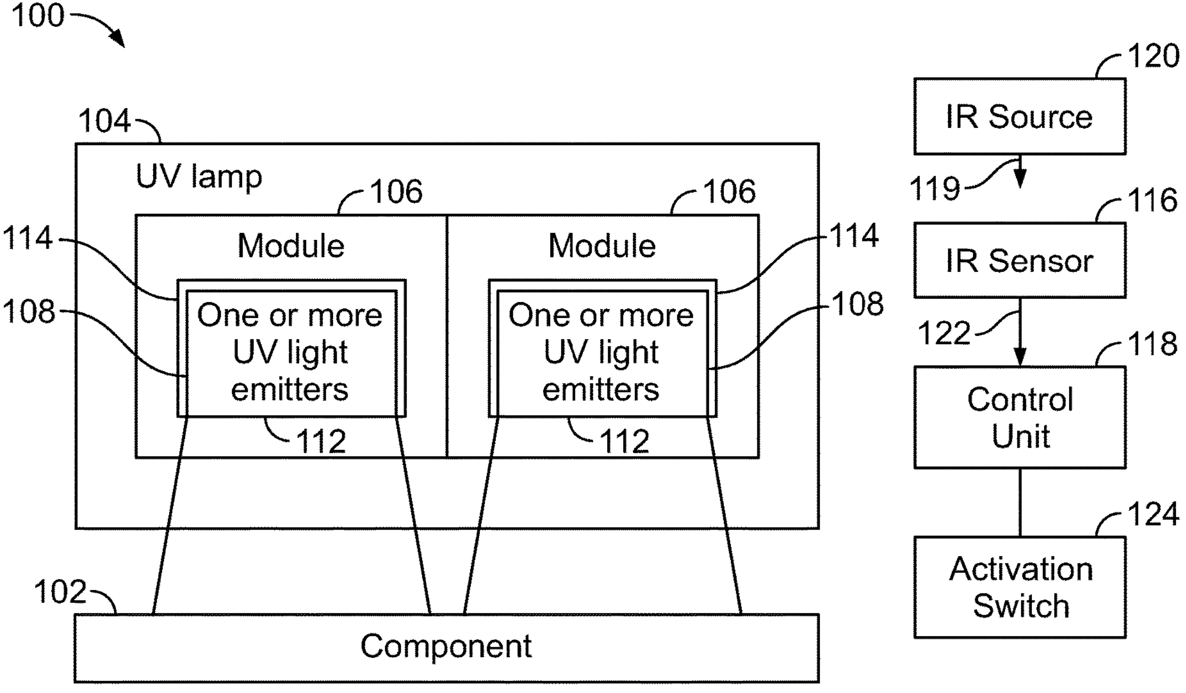
FIG. 1 illustrates a schematic block diagram of a system for disinfecting a component, according to an embodiment of the present disclosure.

The foregoing summary, as well as the following detailed description of certain embodiments will be better understood when read in conjunction with the appended drawings. As used herein, an element or step recited in the singular and preceded by the word “a” or “an” should be understood as not necessarily excluding the plural of the elements or steps. Further, references to “one embodiment” are not intended to be interpreted as excluding the existence of additional embodiments that also incorporate the recited features. Moreover, unless explicitly stated to the contrary, embodiments “comprising” or “having” an element or a plurality of elements having a particular condition can include additional elements not having that condition.

Certain embodiments of the present disclosure provide a system for disinfecting (for example, sanitizing, decontaminating, cleaning, or the like) one or more components. The system includes a plurality of modules coupled together to form a UV lamp. Each of the plurality of modules includes one or more UV light emitters that are configured to emit UV light onto a component to disinfect the component. In at least one embodiment, each of the modules also includes a power supply coupled to the UV light emitters. The modules can also include a band pass filter that is configured to filter the generated UV light from the UV light emitters to a desired wavelength, such as within the far UV spectrum, the UVC spectrum, or the like. In at least one embodiment, different modules can emit UV light at different wavelengths. For example, a first module can emit UV light within the far UV spectrum, while a second module coupled to the first module can emit UV light within the UVC spectrum. Optionally, the system may not include a plurality of modules.

Multiple modules may be coupled together (for example, stacked, ganged, or otherwise connected together) as desired for a greater area of UV coverage. Such configuration can be determined based on the size of the surface to be sanitized. The modules can be coupled together through bonding, one or more mechanical connectors or fasteners, and/or the like.

The UV lamp formed by multiple modules can be customized to fit into desired areas. As such, the UV lamp can be compact and configured to fit into small, confined spaces.

In at least one embodiment, the UV lamp is part of a wand assembly that is configured to be held by an operator. In at least one other embodiment, the UV lamp is a fixture within a space, such as within a lavatory. The UV lamp can be fixed in position within the space. Optionally, the UV lamp can be configured to be moved between a stowed position and a deployed position within the space. As another option, the UV lamp can be removably secured to a securing mount.

In at least one embodiment, the system includes an infrared (IR) sensor in communication with a control unit. The IR sensor is configured to detect IR light, such as a beam of IR light emitted from an IR source, which can be reflected to the IR sensor. In operation, the control unit is also in communication with the one or more UV light emitters. The control unit is configured to selectively activate and deactivate the UV light emitters in response to a signal received from the IR sensor. For example, the control unit prevents activation of the UV light emitters and/or deactivates the UV light emitters in response to the IR sensor not detecting the IR light.

For example, an IR source and/or an IR reflector can be positioned within a location, such as proximate to (for example, on or within a foot or less) a lavatory door. The IR sensor is configured to monitor the IR beam and to detect a change when an occupant crosses a threshold. Additionally the system can include a door sensor (such as a door hall effect sensor) installed on and/or proximate to the door to detect when the door is open or closed. The control unit can also be in communication with the door sensor and is configured to selectively activate and deactivate the UV light emitters in response to one or more IR signals received from the IR sensor and/or the door sensor.

In at least one embodiment, the control unit is configured to deactivate the UV light emitters when an area (such as a lavatory) is occupied, and to activate the UV light emitters when the area is unoccupied. Integrating the IR sensor into the UV lamp reduces cost and installation time.

Certain embodiments of the present disclosure provide a sanitizing system and method that includes an ultraviolet (UV) lamp (such as an excimer lamp having one or more UV light emitters, such as light emitting diodes, bulbs, and/or the like) that emits UV light in a far UV light spectrum, such as at a wavelength of 222 nm, which neutralizes (such as kills) microbes (for example, viruses and bacteria), while posing no risk to humans. Optionally, the UV lamp emits the UV light in the UVC spectrum, such as at a wavelength of 254 nm. The UV lamp may be used within an internal cabin to decontaminate and kill pathogens. The UV lamp may be used in a portable sanitizing system or a fixed sanitizing system. For example, operating the UV lamp to emit sanitizing UV light having a wavelength within the far UV spectrum or UVC spectrum may be used with a portable system or a fixed system.

Certain embodiments of the present disclosure provide a self-contained, universal, modular UV lamp, such as may have one or more modules, that can be secured and mounted at various locations within an area, such as an internal cabin of an aircraft. The UV lamp can be selectively secured and removed from a mounting location. In at least one embodiment, the UV lamp is in communication with a monitoring sub-system that is configured to detect a position of the UV lamp within an area. The monitoring sub-system can further be configured to predict activity in relation to the location of the UV lamp, and control the UV lamp accordingly.

Certain embodiments of the present disclosure provide a UV lamp, which can be portable. In at least one embodiment, the UV lamp includes one or more modules. In at least one embodiment, the UV lamp includes one or more light emitters, a controller, a housing, a memory, a power supply, one or more sensors, one or more indicators, a communication device, a location detection device, and a mounting interface. The UV lamp is configured to be mounted or retrofitted in an area to be disinfected.

In at least one embodiment, the UV lamp is configured to modulate a level of UV irradiance based on occupancy of the area. The UV lamp is configured to determine its location in an area, and communicate with other UV lamps in the same area or to other systems external to the area to manage functions such as power levels, system health, system performance, and system issues.

FIG. 1 illustrates a schematic block diagram of a system 100 for disinfecting a component 102, according to an embodiment of the present disclosure. The component 102 can be any structure that is to be disinfected with UV light. For example, the component 102 can be a structure within a vehicle, a fixed building, or the like. As example, the component 102 can be a passenger seat within a vehicle, a portion of a lavatory (such as a toilet, sink, door handle, and/or the like), a counter or other such surface within a kitchen or galley, and/or the like.

The system 100 includes a UV lamp 104 that includes a plurality of modules 106 coupled together. For example, the UV lamp 104 includes a first module 106 coupled to a second module 106. Optionally, the UV lamp 104 can include more than two modules 106.

Each module 106 includes one or more UV light emitters 108 that are configured to emit UV light through an aperture 112. The UV light emitters 108 can emit UV light within the far UV spectrum, such as between 200 nanometers (nm)-230 nm. For example, the UV light emitters can emit UV light at 222 nm. As another example, the UV light emitters 108 can emit UV light within the UVC spectrum, such as between 230 nm and 280 nm. For example, the UV light emitters can emit UV light at 254 nm. In at least one embodiment, the UV light emitters 108 of the modules 106 emit UV light at the same wavelength. In at least one other embodiment, the UV light emitters 108 of the modules 106 emit UV light at different wavelengths. For example, the UV light emitters 108 of a first module 106 emit UV light within the far UV spectrum, and the UV light emitters 108 of a second module 106 emit UV light within the UVC spectrum, or vice versa.

The modules 106 are coupled together to form the light emitting portion of the UV lamp 104. The modules 106 can be removably coupled together. As such, the UV lamp 104 provides a modular assembly that can be customized to a desired size, shape, and lighting capability. Further, if a module 106 is in need of repair, the module 106 can be removed from the UV lamp 104 and replaced within another module 106. Accordingly, the modules 106 allow for efficient production and maintenance of the UV lamp 104.

In at least one embodiment, portions of the modules 106 are covered with one or more electromagnetic interference (EMI) shields 114. For example, in at least one embodiment, the one or more UV light emitters 108 are surrounded on one or more surfaces with an EMI shield 114, with the aperture 112 being uncovered by the EMI shield 114. In at least one embodiment, the EMI shield 114 is a metal cover, such as a foil formed of aluminum, steel, or the like that covers a housing of the module 106 with the aperture 112 remaining uncovered. Optionally, the modules 106 do not include the EMI shield 114.

The UV lamp 104 can be part of a wand assembly, which is configured to be held by an individual. The wand assembly can be coupled to a backpack assembly, a case assembly, a cart, and/or the like. As another example, the wand assembly can be a standalone assembly that is not coupled to a backpack assembly, a case assembly, a cart, or the like.

As another example, the UV lamp 104 can be a fixture within an area. For example, the UV lamp 104 can be secured within a lavatory, galley, kitchen, or various other areas. The UV lamp 104 can be fixed in position within the area. Optionally, the UV lamp 104 can be moveable between a stowed position and a deployed position within the area. In at least one other embodiment, the UV lamp 104 can be removably securable to various structures, such as securing mounts located within an area, such as within a vehicle.

In at least one embodiment, the system 100 also includes an infrared (IR) sensor 116 in communication with a control unit 118, such as through one or more wired or wireless connections. The control unit 118 is also in communication with the UV light emitters 108 of the modules 106, such as through one or more wired or wireless connections. In at least one embodiment, the UV lamp 104 includes the IR sensor 116 and/or the control unit 118. Optionally, the IR sensor 116 and/or the control unit 118 can be remotely located from the UV lamp 104.

In operation, the control unit 118 selectively activates and deactivates the UV light emitters 108 based on an IR signal emitted by and received from the IR sensor 116. For example, the IR sensor 116 is configured to receive an IR light signal 119 emitted by an IR source 120, either directly from the IR source 120, or indirectly from a reflector that receives and reflects the IR light signal 119 from the IR source 120. When the IR sensor 116 receives the IR light signal 119, the IR sensor 116 outputs a sensed IR signal 122 to the control unit 118. Based on the received sensed IR signal 122, the control unit 118 activates the one or more UV light emitters 108 to emit the UV light. If, however, the IR sensors 116 does not receive the IR light signal 119 (such as if the IR light signal 119 is blocked by an individual), the IR sensor does not output the sensed IR signal 122 to the control unit 118. In response to not receiving the sensed IR signal 122, the control unit 118 deactivates the UV light emitters 108 so that they do not emit the UV light.

In at least one embodiment, an activation switch 124 is in communication with the control unit 118, such as through one or more wired or wireless connections. The activation switch 124 can be secured to the UV lamp 104. That is, the UV lamp 104 can include the activation switch 124. Optionally, the activation switch 124 can be remotely located from the UV lamp 104. When the activation switch 124 is engaged to activate the UV light emitters 108, the control unit 118 operates as explained above (that is, the control unit 118 selectively activates and deactivates the UV light emitters based on the signal received from the IR sensor 116). When the activation switch 124 is disengaged so that the UV light emitters 108 are not to emit the UV light, the control unit 118 maintains the UV light emitters 108 in a deactivated state even if the sensed IR signal 122 is received from the IR sensor 116. Optionally, the system 100 may not include the activation switch.

In at least one embodiment, the system 100 includes the UV lamp 104 having UV light emitters 108 whether or not within the modules 106. For example, the UV lamp 104 can be a single, non-modular assembly that is in communication with the control unit 118, which selectively activates and deactivates the UV light emitters 108 as described herein. In at least one other embodiment, the system 100 does not include the IR sensor 116 or the IR source 120.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the control unit 118 may be or include one or more processors that are configured to control operation, as described herein.

The control unit 118 is configured to execute a set of instructions that are stored in one or more data storage units or elements (such as one or more memories), in order to process data. For example, the control unit 118 may include or be coupled to one or more memories. The data storage units may also store data or other information as desired or needed. The data storage units may be in the form of an information source or a physical memory element within a processing machine.

The set of instructions may include various commands that instruct the control unit 118 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the control unit 118. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control unit 118 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 2:
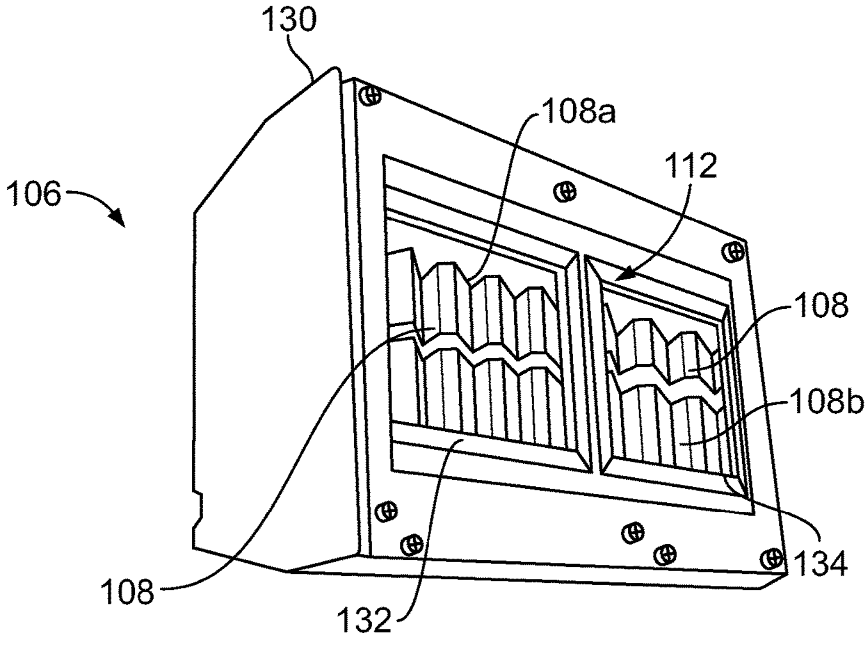
FIG. 2 illustrates a perspective bottom view of a module, according to an embodiment of the present disclosure.

FIG. 2 illustrates a perspective bottom view of a module 106, according to an embodiment of the present disclosure. The module 106 includes a housing 130 that retains a plurality of UV light emitters 108 that are configured to emit UV light through the aperture 112. As shown, the module 106 includes a first plurality of UV light emitters **108*a* and a second plurality of UV light emitters 108*b*. The first plurality of UV light emitters 108*a* are contained within a first sub-housing 132, and the second plurality of UV light emitters 108*b* are contained within a second sub-housing 134 that is distinct from the first sub-housing 132. Each of the first sub-housing 132 and the second sub-housing 134 can contain more or less UV light emitters 108 than shown. Optionally, the module 106 can include a single sub-housing that retains all of the UV light emitters 108 shown in FIG. 2. In at least one embodiment, the module 106 can include a single UV light emitter 108, instead a plurality of UV light emitters 108**.

Figure 3:
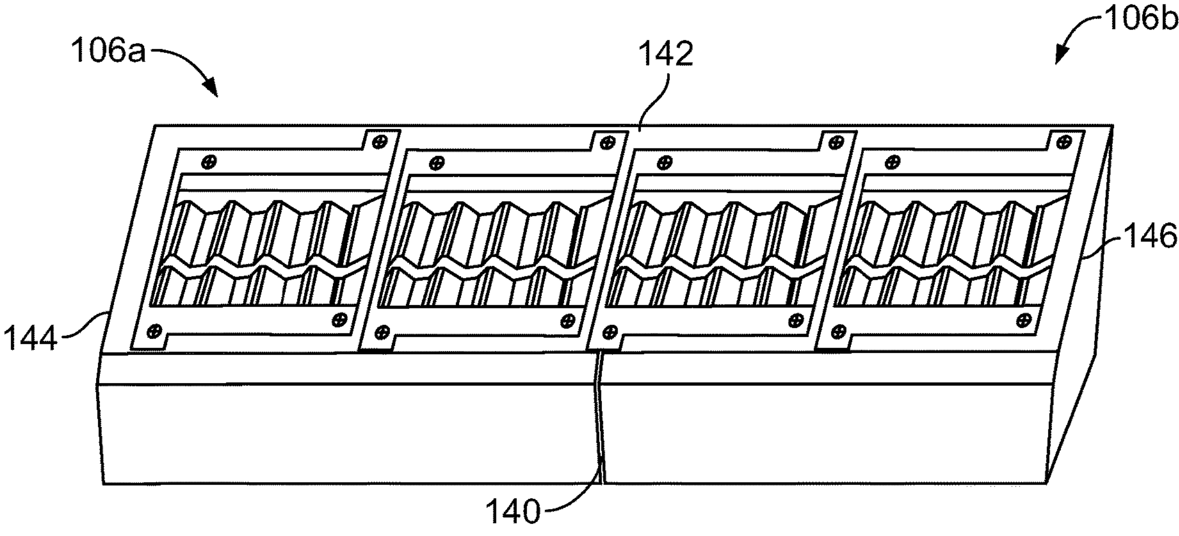
FIG. 3 illustrates a perspective bottom view of a first module coupled to a second module, according to an embodiment of the present disclosure.

FIG. 3 illustrates a perspective bottom view of a first module **106*a* coupled to a second module 106*b*, according to an embodiment of the present disclosure. A first end 140 of the first module 106*a* is coupled to an opposite second end 142 of the second module 106*b*. Optionally, the first module 106*a* and the second module 106*b* can be coupled together in a side-to-side fashion. Another module (not shown in FIG. 3) can be coupled to a second end 144 of the first module 106*a*. Further, another module (not shown in FIG. 3) can be coupled to a first end 146 of the second module 106*b***.

The modules **106*a* and 106*b*, as well as additional modules, can be stacked end-to-end, and/or side-to-side, as desired, to provide various illumination patterns. The first module 106*a* and the second module 106*b* can be removably coupled together, such as through one or more fasteners, bonding, a dove tail joint, a lap joint, a plug and socket connection, and/or the like. As such, the first module 106*a* and the second module 106*b* can be efficiently coupled together. Further, the first module 106*a* and the second module 106*b* can be disconnected, such as if one of the first module 106 or the second module 106*b*** is in need of repair or is to be replaced.

Figure 4:
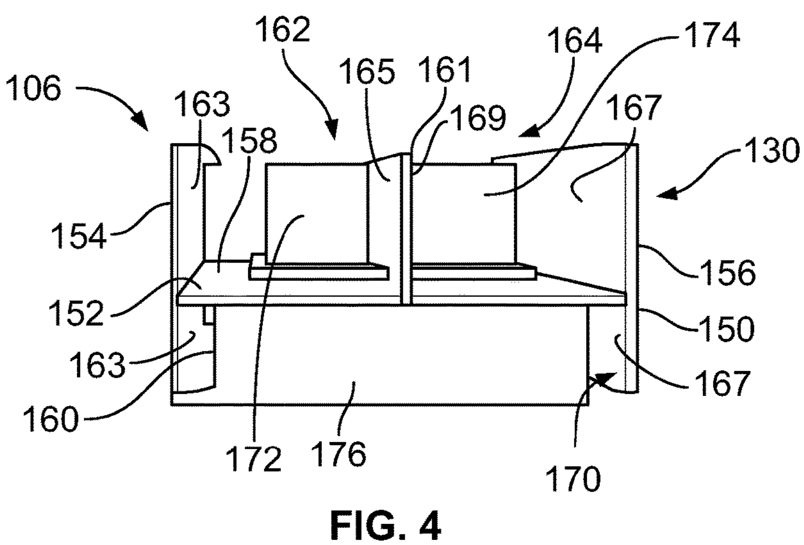
FIG. 4 illustrates a perspective end view of a module, according to embodiment of the present disclosure.
Figure 5:
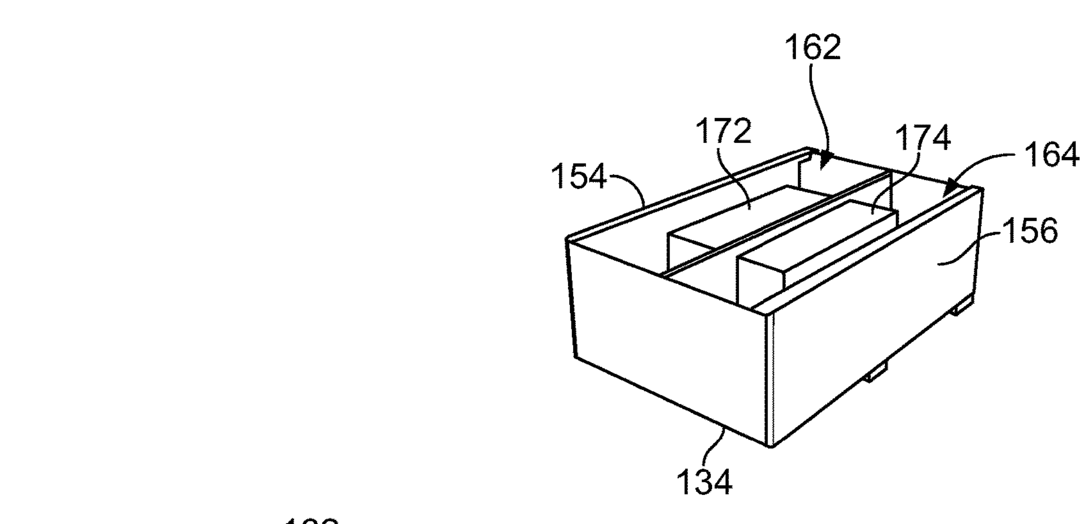
FIG. 5 illustrates a perspective top view of the module of FIG. 4.
Figure 6:
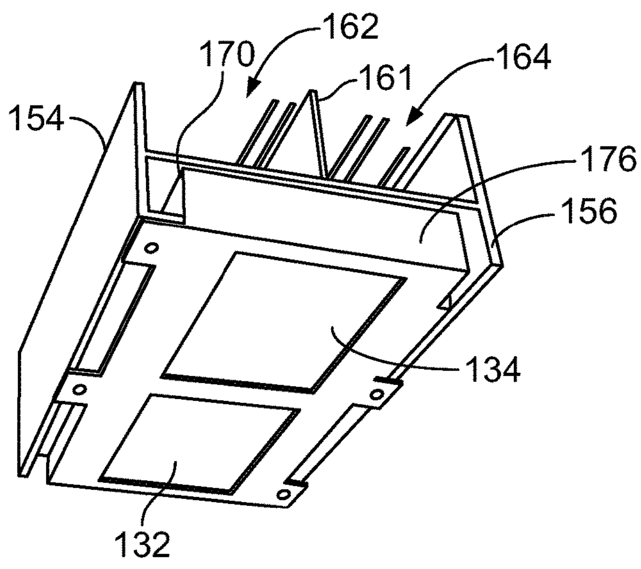
FIG. 6 illustrates a perspective bottom view of the module of FIG. 4.

FIG. 4 illustrates a perspective end view of a module 106, according to embodiment of the present disclosure. FIG. 5 illustrates a perspective top view of the module 106 of FIG. 4. FIG. 6 illustrates a perspective bottom view of the module 106 of FIG. 4. Referring to FIGS. 4-6, for the sake of clarity, certain outer wall portions of the module 106 are not shown in order show internal components.

In at least one embodiment, the housing 130 includes a bracket 150 having a platform 152 extending between opposite side walls 154 and 156. The platform 152 includes an upper surface 158 opposite from a lower surface 160. A dividing wall 161 upwardly extends from the upper surface 156. A first power chamber 162 is defined between the upper surface 158, an interior surface 163 of the side wall 154, and a first side surface 165 of the dividing wall 161. A second power chamber 164 is defined between the upper surface 158, an interior surface 167 of the side wall 156, and a second side surface 169 (opposite from the first side surface 165) of the dividing wall 161. An emitter chamber 170 is defined between the lower surface 158, the interior surface 163 of the side wall 154, and the interior surface 167 of the side wall 156.

A first power supply 172 is secured within the first power chamber 162. A second power supply 174 is secured within the second power chamber 164. Referring to FIGS. 1-6, the first power supply 172 and the second power supply 174 may be batteries and/or electrical power interfaces, connections, and/or the like that are configured to provide power to the UV light emitters 108.

In at least one embodiment, a frame 176 is secured within the emitter chamber 170, such as via one or more fasteners, bonding, and/or the like. The frame 176 retains the first sub-housing 132 and the second sub-housing 134. The UV light emitters 108 of the first sub-housing 132 and the second sub-housing 134 are electrically coupled to the first power supply 172 and the second power supply 174, respectively, such as through wires that pass through slots, channels, or other such openings formed in the platform 152.

The platform 152 separates and isolates the frame 176 (including the UV light emitters 108) from the first power supply 172 and the second power supply 174. Further, the dividing wall 161 separates and isolates first power supply 172 from the second power supply 174. In at least one embodiment, the first power supply 172 and the second power supply 174 can be high voltage power supplies (such as 2 kV), and therefore the separation and isolation therebetween and in relation to the frame 176 ensures reliable and efficient operation.

As shown, the first power supply 172 and the second power supply 174 are stacked above the frame 176, which retains the first sub-housing 132 and the second sub-housing 134. Optionally, a single power supply can be used to provide power to the UV light emitters 108 of the first sub-housing 132 and the second sub-housing 134. In at least one embodiment, the bracket 150 may not include the dividing wall 161. In at least one other embodiment, the power suppl(ies) can be remote from the module 106.

Figure 7:
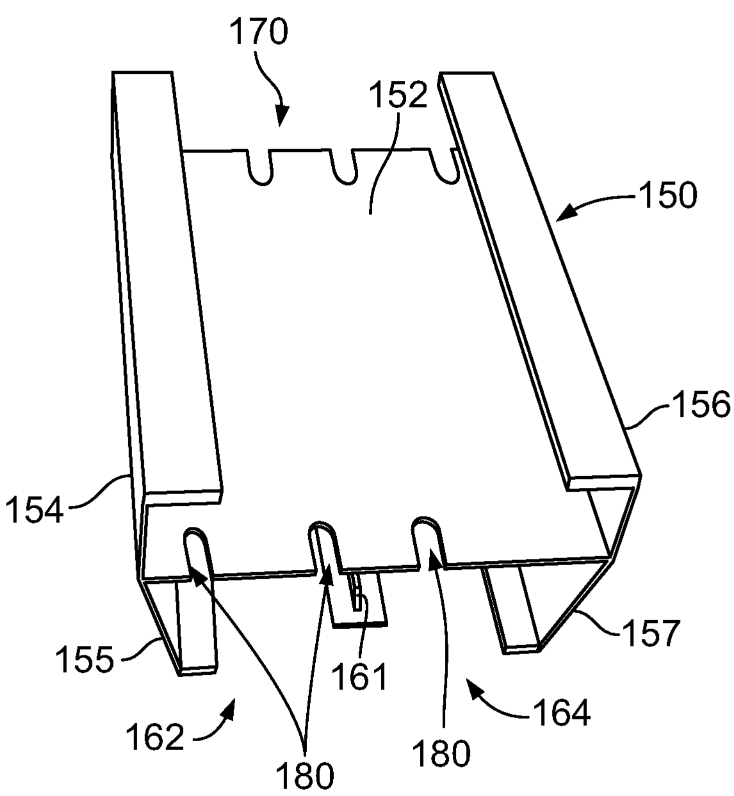
FIG. 7 illustrates a perspective bottom view of a bracket, according to an embodiment of the present disclosure.
Figure 8:
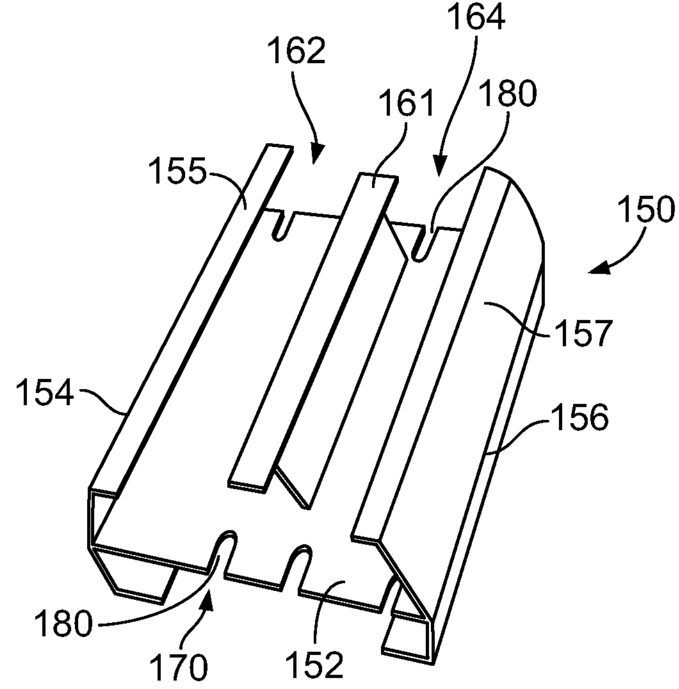
FIG. 8 illustrates a perspective top view of the bracket of FIG. 7.

FIG. 7 illustrates a perspective bottom view of the bracket 150, according to an embodiment of the present disclosure. FIG. 8 illustrates a perspective top view of the bracket 150 of FIG. 7. Referring to FIGS. 7 and 8, the bracket 150 can include one or more passages 180 (such as slots) formed through the platform 152. Referring to FIGS. 1-8, the passages 180 allow for wiring to be routed between the UV light emitters 108 and the power supplies 172 and/or 174, for example. Optionally, the bracket 150 may not include the passages 180. Instead, wiring can be routed around end edges of the platform 152, for example.

As shown, the side walls 154 and 156 can includes inwardly-canted segments 155 and 157, respectively, bounding the first power chamber 162 and the second power chamber 164, respectively. Free ends of the inwardly-canted segments angle toward the dividing wall 161. The inwardly-canted segments 155 and 157 provide a more compact bracket 150, which takes up less space. Optionally, the side walls 154 and 156 can also, or alternatively, include inwardly-canted segments. Alternatively, the bracket 150 may not include inwardly-canted segments.

Figure 9:
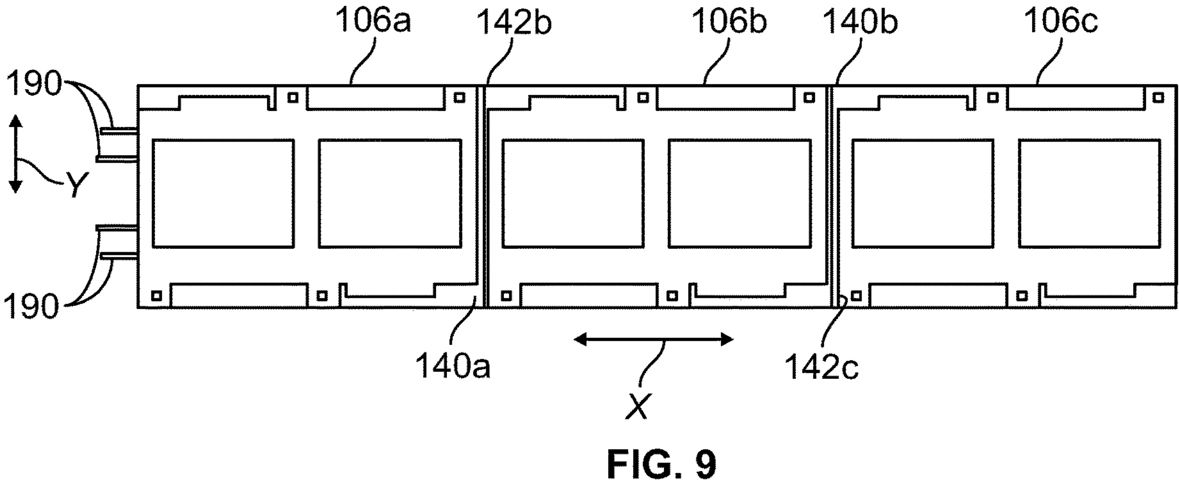
FIG. 9 illustrates a bottom view of a plurality of modules coupled together, according to an embodiment of the present disclosure.

FIG. 9 illustrates a bottom view of a plurality of modules 106*a*, 106*b*, and 106*c* coupled together, according to an embodiment of the present disclosure. A first end 140*a* of the module 106*a* is secured to a second end 142*b* of the module 106*b*. A first end 140*b* of the module 106*b* is secured to a second end 142*c* of the module 106*c*. As shown, the modules 106*a*, 106*b*, and 106*c* are linearly aligned in the X direction in an end-to-end configuration. Optionally, one or more of the modules 106*a*, 106*b*, and 106*c* can be aligned in the Y direction a side-to-side configuration. Wiring 190 is routed to each of the modules 106*a*, 106*b*, and 106*c*.

Figure 10:
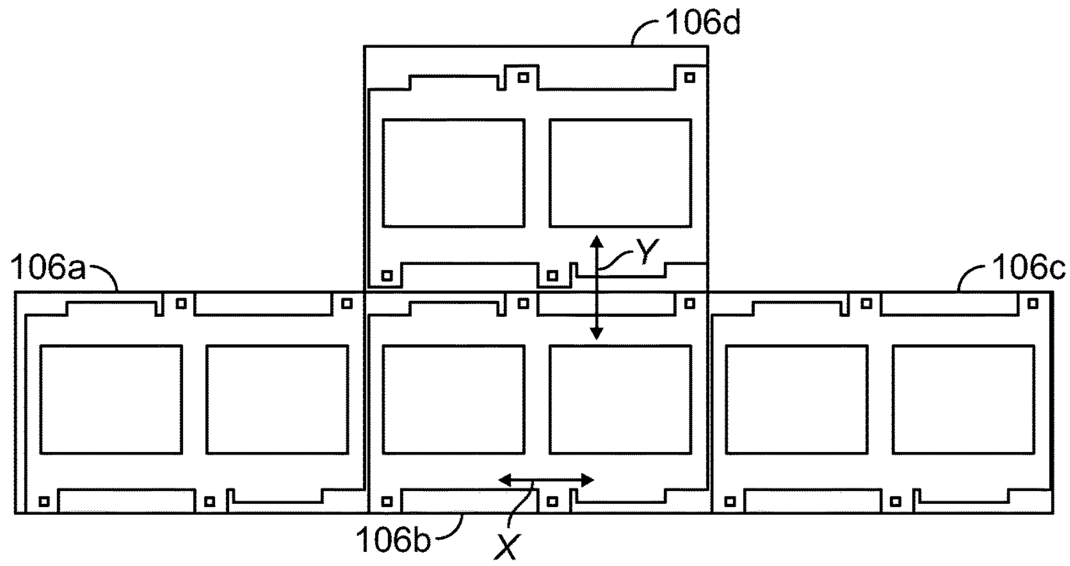
FIG. 10 illustrates a bottom view of a plurality of modules coupled together, according to an embodiment of the present disclosure.

FIG. 10 illustrates a bottom view of a plurality of modules 106*a*, 106*b*, 106*c*, and 106*d* coupled together, according to an embodiment of the present disclosure. As shown, the module 106*d* can be secured to the module 106*b* in a side-to-side fashion. Optionally, the module 106*d* can be coupled to the module 106*a* or 106*c*. In at least one other embodiment, additional modules (not shown) can be coupled to each of the modules 106*a*, 106*b*, or 106*c* in a side-to-side configuration.

Figure 11:
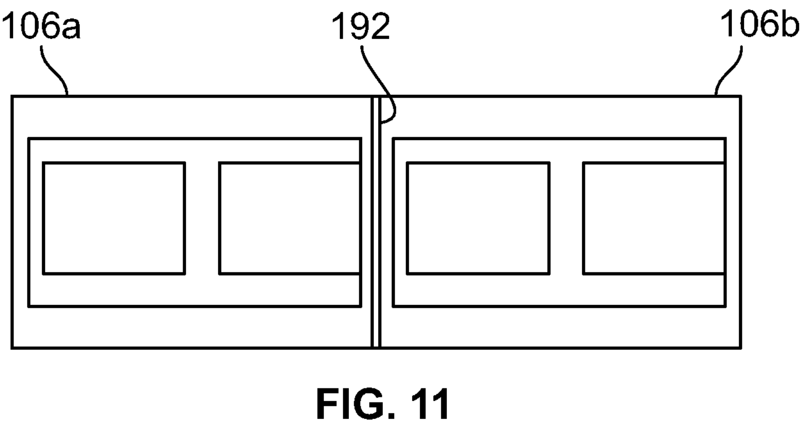
FIG. 11 illustrates a bottom view of a first module coupled to a second module, according to an embodiment of the present disclosure.

FIG. 11 illustrates a bottom view of a first module 106*a* coupled to a second module 106*b*, according to an embodiment of the present disclosure. The first module 106*a* couples to the second module 106*b* via bonding at a bond interface 192 therebetween.

Figure 12:
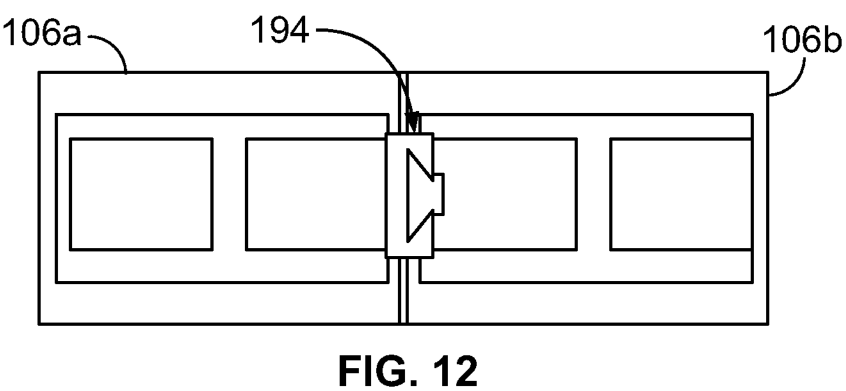
FIG. 12 illustrates a bottom view of a first module coupled to a second module, according to an embodiment of the present disclosure.

FIG. 12 illustrates a bottom view of a first module 106*a* coupled to a second module 106*b*, according to an embodiment of the present disclosure. The first module 106*a* couples to the second module 106*b* via a connecting joint 194, such as a dove tail joint.

Figure 13:
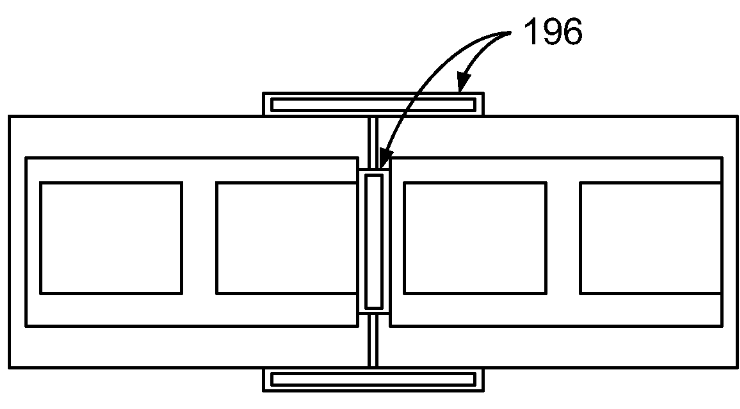
FIG. 13 illustrates a bottom view of a first module coupled to a second module, according to an embodiment of the present disclosure.

FIG. 13 illustrates a bottom view of a first module 106*a* coupled to a second module 106*b*, according to an embodiment of the present disclosure. The first module 106*a* couples to the second module 106*b* via one or more connecting joints 196, such as lap toil joints at connected ends and/or sides. Fasteners, such as screws or bolts, and/or bonding can be used to secure the connecting joints 196 to the first module 106*a* and the second module 106*b*.

Figures 14, 15:
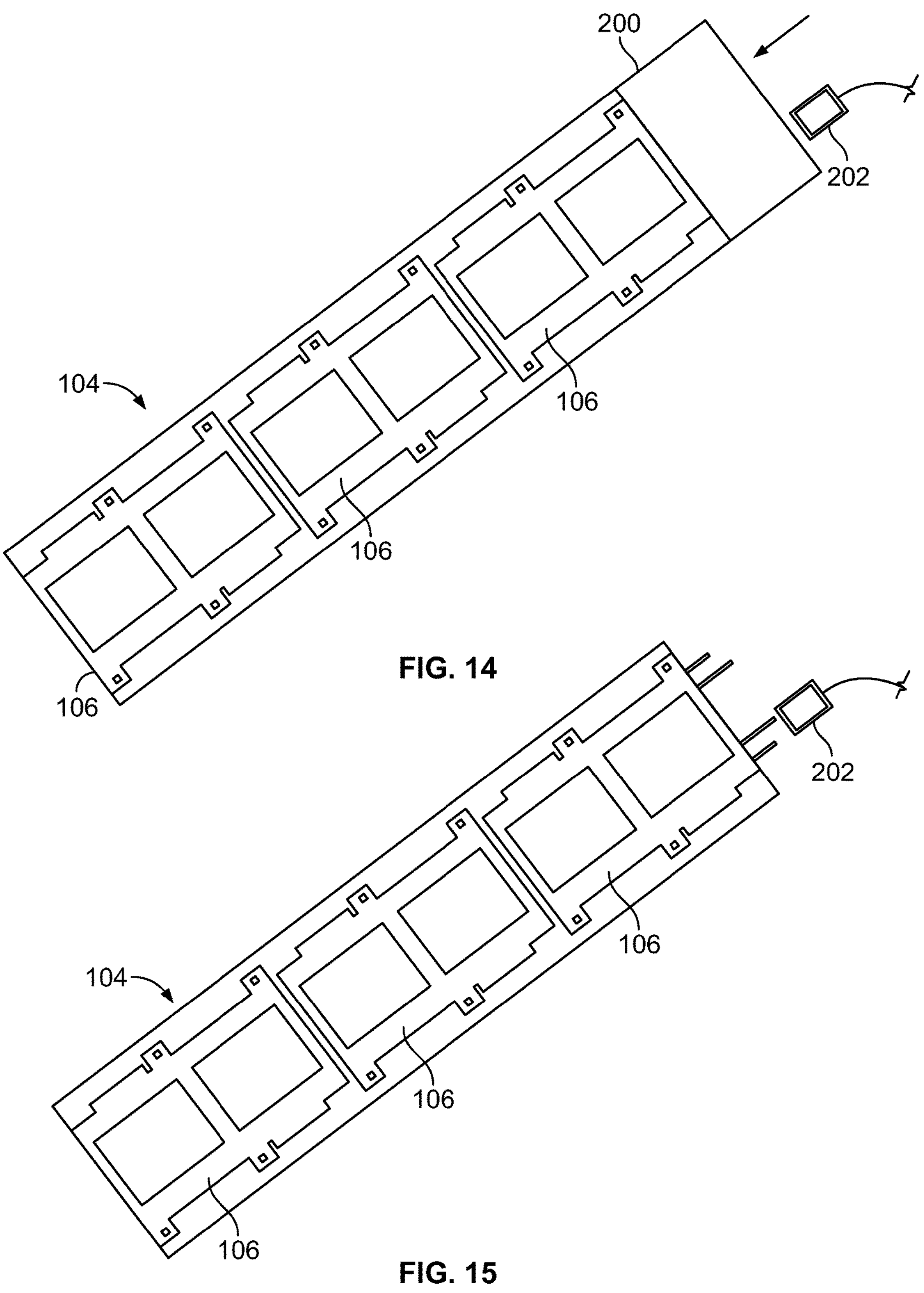
FIG. 14 illustrates a bottom view of a UV lamp having a plurality of modules, according to an embodiment of the present disclosure.
FIG. 15 illustrates a bottom view of a UV lamp having a plurality of modules, according to an embodiment of the present disclosure.

FIG. 14 illustrates a bottom view of the UV lamp 104 having a plurality of modules 106, according to an embodiment of the present disclosure. The UV lamp 104 can include a battery 200, such as 24 V battery, that provides power to the power supplies of the modules 106. In at least one embodiment, the battery 200 is configured to mate with a power cord 202 to be recharged.

FIG. 15 illustrates a bottom view of the UV lamp 104 having a plurality of modules 106, according to an embodiment of the present disclosure. In this embodiment, the UV lamp 104 may not include a battery. Instead, the UV lamp receives power from the power cord 202.

Figure 16:
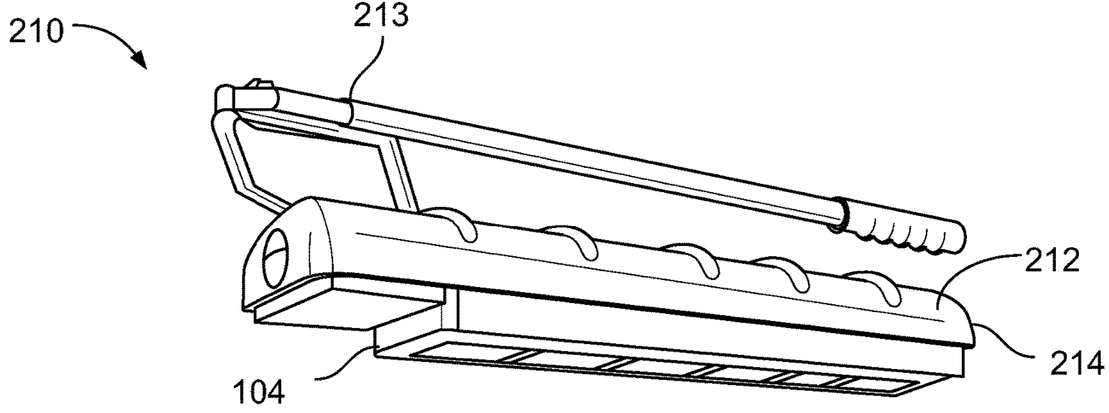
FIG. 16 illustrates a perspective lateral view of a wand assembly including a UV lamp, according to an embodiment of the present disclosure.
Figure 17:
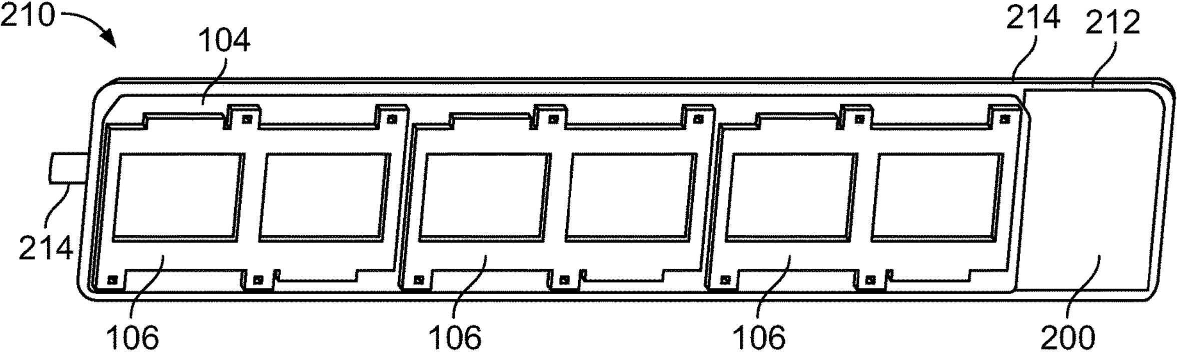
FIG. 17 illustrates a bottom view of the wand assembly of FIG. 16.

FIG. 16 illustrates a perspective lateral view of a wand assembly 210 including the UV lamp 104, according to an embodiment of the present disclosure. FIG. 17 illustrates a bottom view of the wand assembly of FIG. 16. Referring to FIGS. 16 and 17, the wand assembly 210 includes a sanitizing head 212 coupled to a handle 213. The sanitizing head 212 includes a shroud 214 that retains the UV lamp 104. The battery 200 can be retained within the shroud 214.

In at least one embodiment, the sanitizing head 212 is configured to move relative to the handle 213. For example, the sanitizing head 212 can be extended and/or rotated relative to the handle 213. In at least one other embodiment, the sanitizing head 212 is fixed in relation to the handle 213. The wand assembly 210 can include the UV lamp 104 having a plurality of modules 106, as described with respect to any of FIGS. 1-15.

Figure 18:
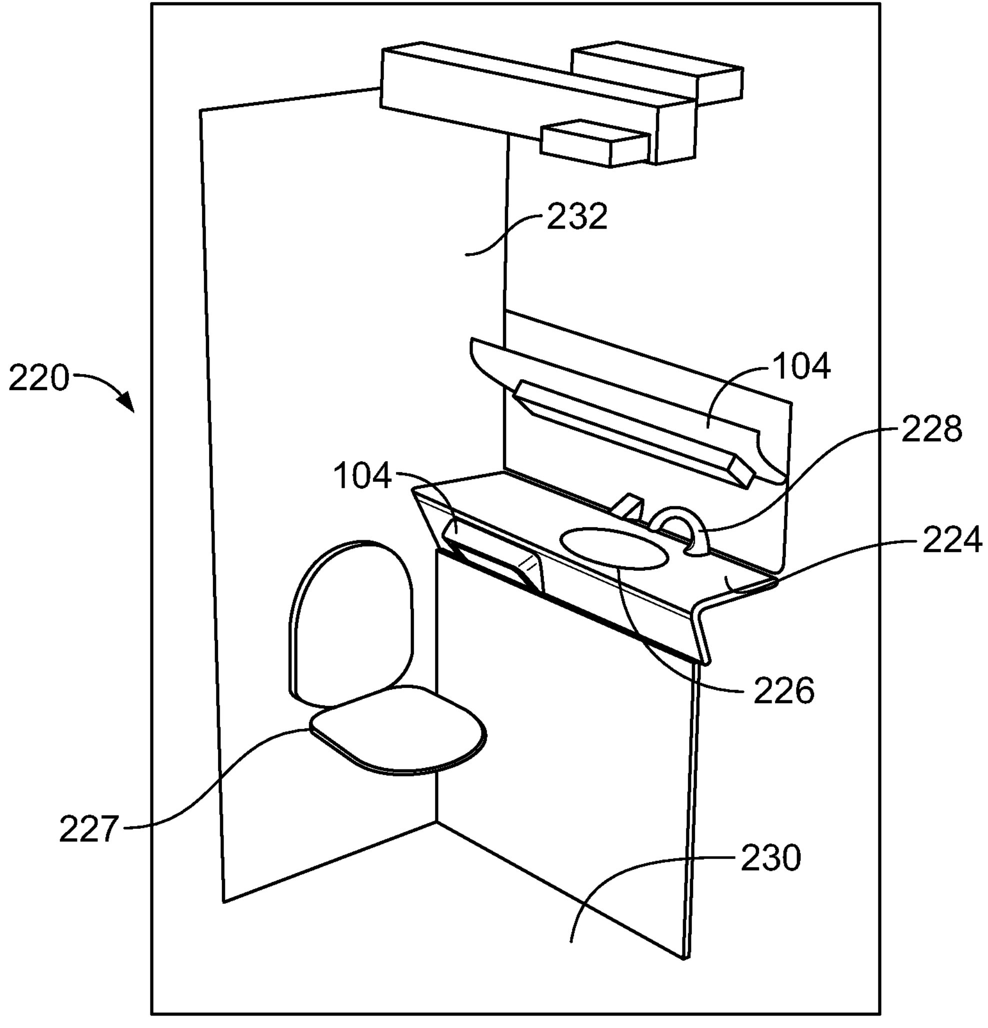
FIG. 18 illustrates a perspective internal view of a lavatory, according to an embodiment of the present disclosure.

FIG. 18 illustrates a perspective internal view of a lavatory 220, according to an embodiment of the present disclosure. The lavatory 220 may be within an internal cabin of a vehicle, such as a commercial aircraft. The lavatory 220 includes a toilet 222 and a counter 224 having a sink 226 and faucet 228. One or more UV lamps 104 are disposed within the lavatory 220. The UV lamps 104 are configured as described with respect to any of FIGS. 1-15.

The UV lamps 104 are configured to emit UV light to disinfect one or more components within the lavatory 220, such as the toilet 222, the counter 224, the sink 226, the faucet 228, the floor 230, one or more walls 232, and/or the like. In at least one embodiment, the UV lamps 104 can be fixed in position. In at least one other embodiment, the UV lamps 104 can be configured to move. For example, the UV lamps 104 can be moved between stowed positions and deployed positions.

Figure 19:
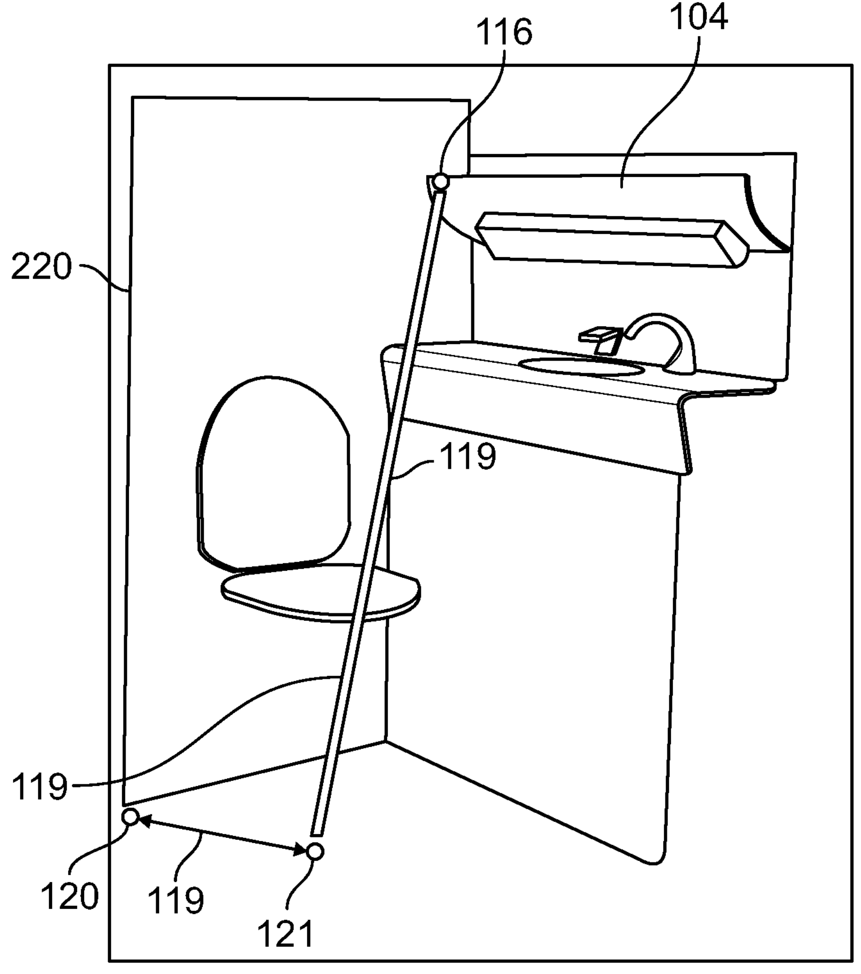
FIG. 19 illustrates a perspective internal view of the lavatory, according to an embodiment of the present disclosure.

FIG. 19 illustrates a perspective internal view of the lavatory 220, according to an embodiment of the present disclosure. Referring to FIGS. 1 and 19, in this embodiment, the UV lamp 104 includes the IR sensor 116 that receives the IR light signal 119 from the IR source 120. The IR source 120 is configured to emit the IR light signal 119 through an area in which an individual would be if occupying the lavatory 220.

The IR sensor 116 may be aligned with the IR source 120 to directly receive the IR light signal 119 from the IR source 120. Optionally, the IR source 120 may be configured to emit the IR light signal 119 at a reflector, such as a mirror, that reflect the IR light signal 119 to the IR source 120.

The IR sensor 116 can be mounted directly to the UV lamp 104, such as on a housing. In at least one embodiment, the IR sensor 116 can be secured to a module 106. In at least one embodiment, multiple modules 106 include an IR sensor 116. In at least one other embodiment, the IR sensor 116 is remote from the UV lamp 104.

As shown, the IR sensor 116 can be secured to an end or corner of the UV lamp 104. The IR sensor 116 is configured to receive the IR light signal 119 either directly from the IR source 120 or indirectly from the IR source 120 as reflected from one or more reflectors 121. The IR light signal 119 can be a laser or narrow non-laser optical signal, for example.

As shown, the IR light signal 119 is configured to extend through a portion of the lavatory 220 such that a person entering or exiting the room crosses the path of and interrupts the IR light signal 119. As the path between the IR source 120 and the IR sensor 116 is interrupted, the IR sensor 116 does not receive the IR light signal 119. When the IR sensor 116 does not receive the IR light signal 119, the control unit 118 does not receive the sensed IR signal 122 from the IR sensor 116. Further, the IR light signal 119 is directed such that an individual within the lavatory 220 would interrupt the IR light signal 119.

Figure 23:
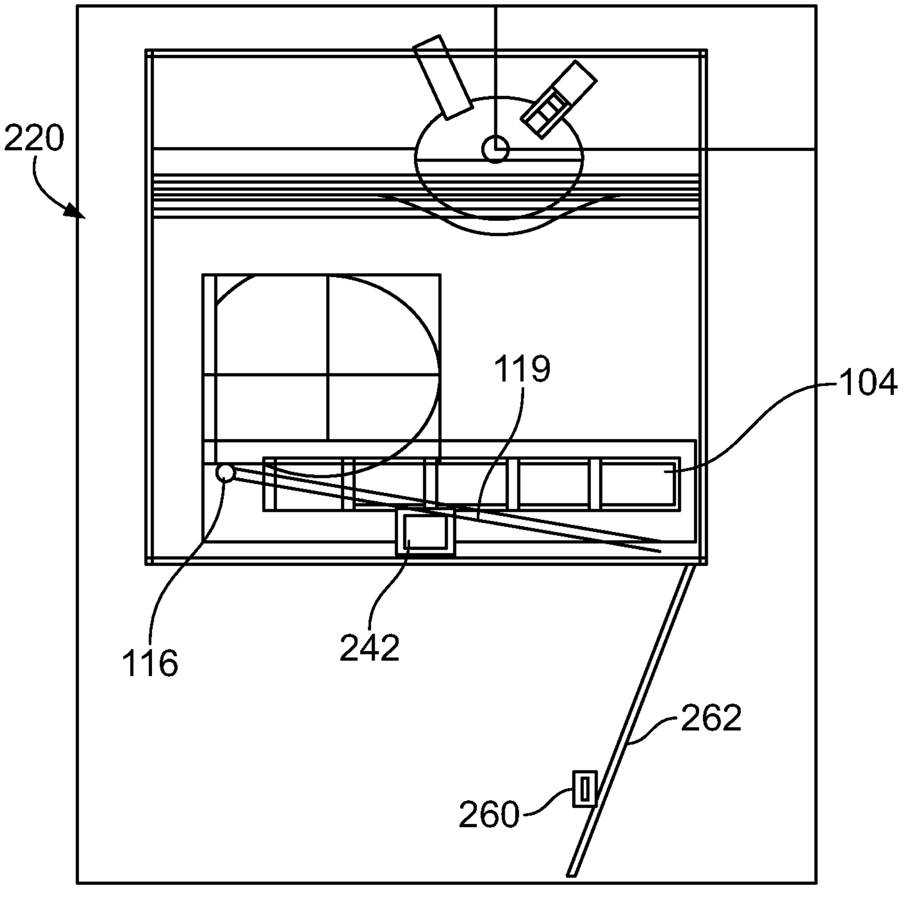
FIG. 23 illustrates a top plan view of a lavatory, according to an embodiment of the present disclosure.
Figure 24:
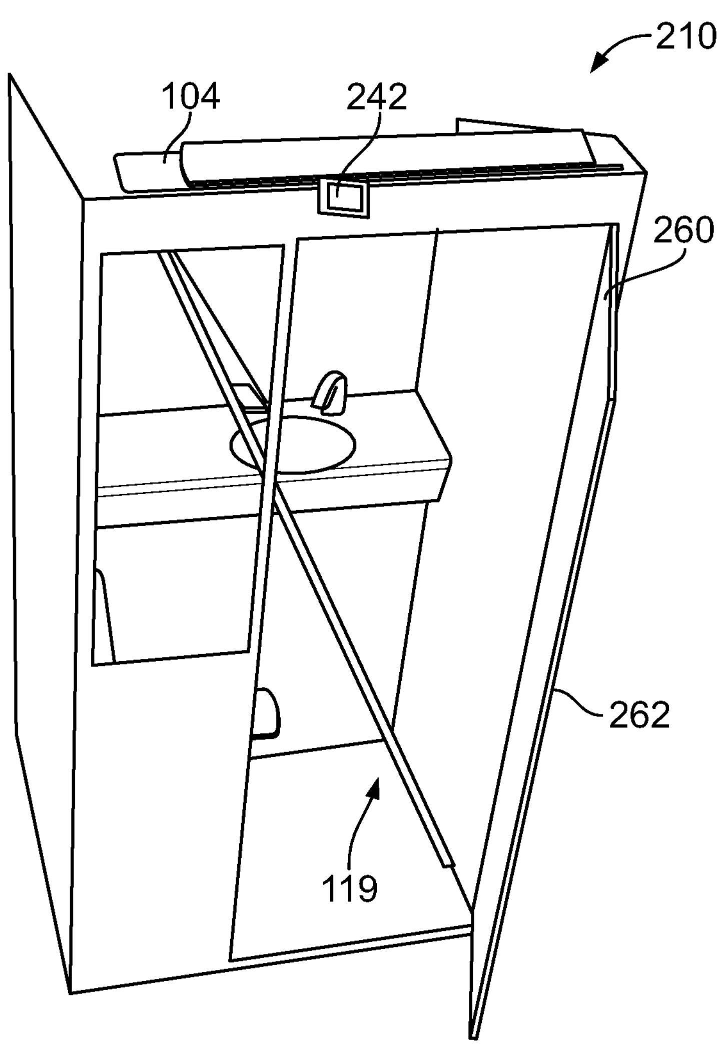
FIG. 24 illustrates a perspective internal view of the lavatory of FIG. 23.

The control unit 118 operates to ensure that the UV light emitters 108 are deactivated when an individual is within the lavatory 220 (or other such room in which the UV lamp 104 is used). By communicating with the IR sensor 116 (and optionally, the door sensor 242 as shown in FIGS. 23 and 24), the control unit 118 determines whether the room is occupied or unoccupied. If occupied, the control unit 118 deactivates the UV light emitters 108. If unoccupied, the control unit 118 can activate the UV light emitters 108 to disinfect one or more components within the room.

FIG. 20 illustrates a perspective bottom view of the UV lamp 104, according to an embodiment of the present disclosure. Referring to FIGS. 1 and 2, the UV lamp 104 104 includes a housing 240 having a plurality of UV light emitters 108, whether within modules 106 or not. The IR sensor 116 is secured to the housing 240 and is oriented in a direction to receive the IR light signal 119.

The control unit 118 is in communication with the IR sensor 116 and the UV light emitters 108. In at least one embodiment, a door sensor 242 is also in communication with the control unit 118, such as through one or more wired or wireless connections. For example, the door sensor 242 is a Hall-effect sensor. The door sensor 242 is configured to detect opening and closing of a door of a room, such as the lavatory 220 shown in FIGS. 18 and 19. The control unit 118 selectively activates and deactivates the UV light emitters 108 based on IR signals (for example reception of such IR signal(s) and lack of reception of such IR signal(s) received from the IR sensor 116 and door signals (for example, signals indicating that the door is open or closed) received from the door sensor 242. Optionally, the control unit 118 is not in communication with a door sensor.

FIG. 21 illustrates a perspective bottom view of the UV lamp 104, according to an embodiment of the present disclosure. In this embodiment, the IR sensor 116 is remotely located from the UV lamp 104, and is in communication with the control unit 118 through one or more wired or wireless connections.

FIG. 22 illustrates a perspective bottom view of the UV lamp 104, according to an embodiment of the present disclosure. As shown, the housing 240 can include an extension 245. The IR sensor 116 can be mounted on the extension 245.

FIG. 23 illustrates a top plan view of the lavatory 220, according to an embodiment of the present disclosure. FIG. 24 illustrates a perspective internal view of the lavatory 220 of FIG. 23. Referring to FIGS. 1 and 19-24, the door sensor 242, such as a Hall effect sensor, is configured to cooperate with a magnet 260 positioned on the door 262 of the lavatory 220 to determine when the door 262 is opened or closed. For example, when the magnet 260 touches or is in close proximity (such as within 6 inches or less) of the door sensor 242, the door sensor 242 outputs a signal to the control unit 118 that the door 262 is closed. In at least one embodiment, the door sensor 242 can be secured to the housing 240 of the UV lamp 104.

In at least one embodiment, the control unit 118 deactivates the UV light emitters 108 of the UV lamp 104 in response to the IR sensor 116 not receiving the sensed IR signal 122 from the IR sensor 116. Conversely, the control unit 118 activates the UV light emitters 108 to disinfect one or more components within the lavatory 220 in response to receiving the sensed IR signal 122 from the IR sensor 116 and receiving a signal from the door sensor 242 indicating that the door 262 is closed. In at least one embodiment, in response to receiving a signal from the door sensor 242 indicating that the door 262 is opened, the control unit 118 deactivates the UV light emitters 108, even if the control unit 118 receives the sensed IR signal 122 from the IR sensor 116.

Figure 25:
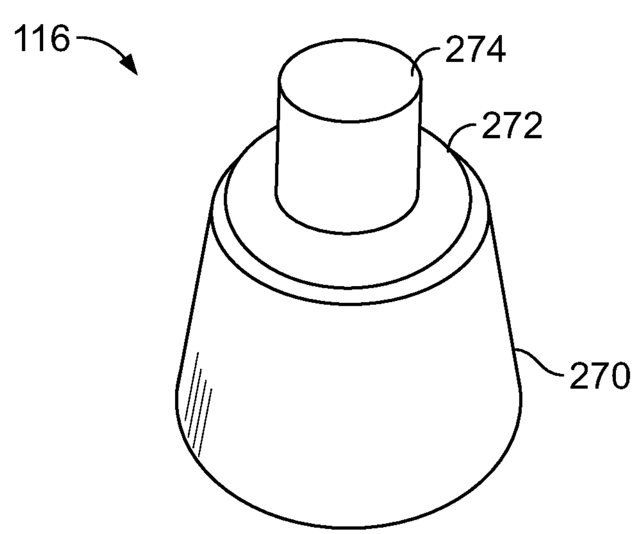
FIG. 25 illustrates a perspective view of an infrared sensor, according to an embodiment of the present disclosure.

FIG. 25 illustrates a perspective view of the IR sensor 116, according to an embodiment of the present disclosure. In at least one embodiment, the IR sensor 116 includes a socket 270 that moveably retains a ball 272. The ball 272 retains a sensing element 274 that is configured to receive and detect an IR light signal. The ball and socket configuration shown in FIG. 25 allows the sensing element 274 to be moved to a desired orientation and alignment so as to receive the IR light signal. Optionally, the IR sensor 116 may not include a moveable element, such as the ball 272 moveably retained within the socket 270.

Referring to FIGS. 1 and 19-25, in at least one embodiment, the control unit 118 activates the UV light emitters 108 in response to determining that the lavatory 220 (or other such room) is vacated and unoccupied. For example, in response to reception of a signal from the door sensor 242 that the door 262 is opened and the sensed IR light signal 122 for at least one second, followed by reception of a signal from the door sensor 242 that the door 262 is closed and the sensed IR light signal 122 for at least one additional second, the control unit 118 activates the UV light emitters 108 for a predetermined sanitizing period (such as 5 seconds). If the control unit 118 detects that the door 262 is opened during the sanitizing period, the control unit 118 immediately deactivates the UV light emitters 108.

Further, if the control unit 118 detects that IR sensor 116 is not receiving the IR light signal 119 (such as by not receiving the sensed IR light signal 122 from the IR sensor), the control unit 118 deactivates the UV light emitters 108. Such an interruption of the IR light signal 119 triggers a reset event, in which the control unit 118 may then reactivate the UV light emitters 108 after determining that the door 262 has been opened, reception of the sensed IR light signal 122 from the IR sensor 116, the door 262 is subsequently closed, and further reception of the sensed IR light signal 122 from the IR sensor 116.

Figure 26:
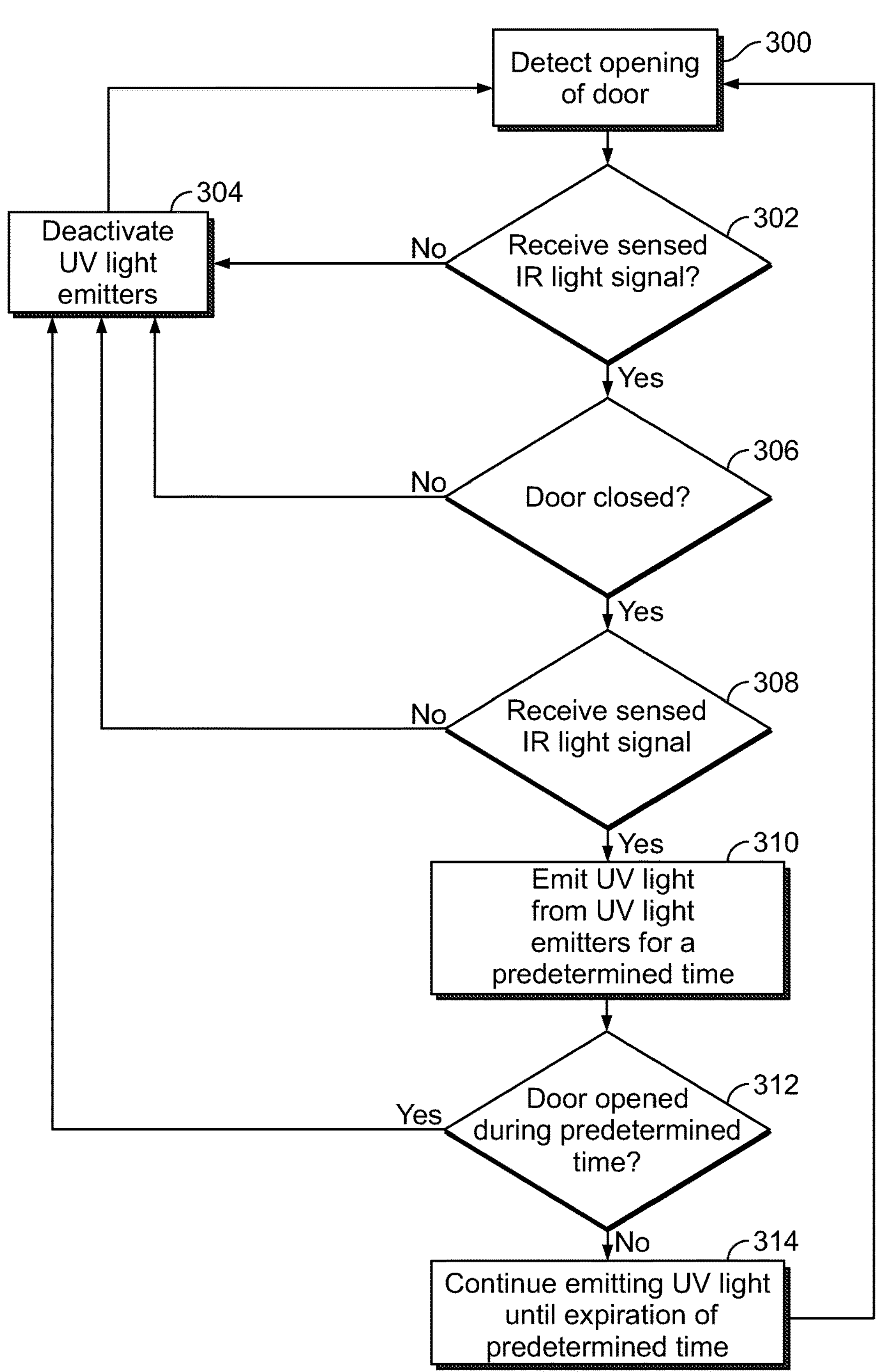
FIG. 26 illustrates a flow chart of a method of operating a UV lamp, according to an embodiment of the present disclosure.

FIG. 26 illustrates a flow chart of a method of operating a UV lamp, according to an embodiment of the present disclosure. Referring to FIGS. 1 and 19-26, at 300, the control unit 118 determines an opening of the door 262, such as via a signal received from the door sensor 242. At 302, the control unit 118 determines if the sensed IR light signal 122 is received from the IR sensor 116. If not, the method proceed to 304, at which the control unit 118 deactivates the UV light emitters 108, and the method then returns to 300.

If, however, the sensed IR light signal 122 is received from the IR sensor 116 at 302, the control unit 118 determines if the door 262 is closed, such as via a signal received from the door sensor 242. If the door is not closed, the method returns to 304.

If, however, the door 262 is closed, the control unit 118 determines if the sensed IR light signal 122 is received at 308. If not, the method returns to 304.

If, however, the control unit 118 determines that the sensed IR light signal 122 is received at 308, the control unit 118 operates the UV lamp 104 at 310 to emit the UV light from the UV light emitters 108 for a predetermined sanitizing time (such as 3-5 seconds). If, at 312, the control unit 118 determines that the door 262 is opened during the predetermined sanitizing time, the method returns to 304, at which the control unit 118 immediately deactivates the UV light emitters 304.

If, however, the door is not opened during the predetermined sanitizing time at 312, the method proceeds from 312 to 314, at which the control unit 118 operates the UV light emitters 108 to continue to emit the UV light until an expiration of the predetermined time, at which point the UV light emitters 108 are deactivated. The process then returns to 300.

Figure 27:
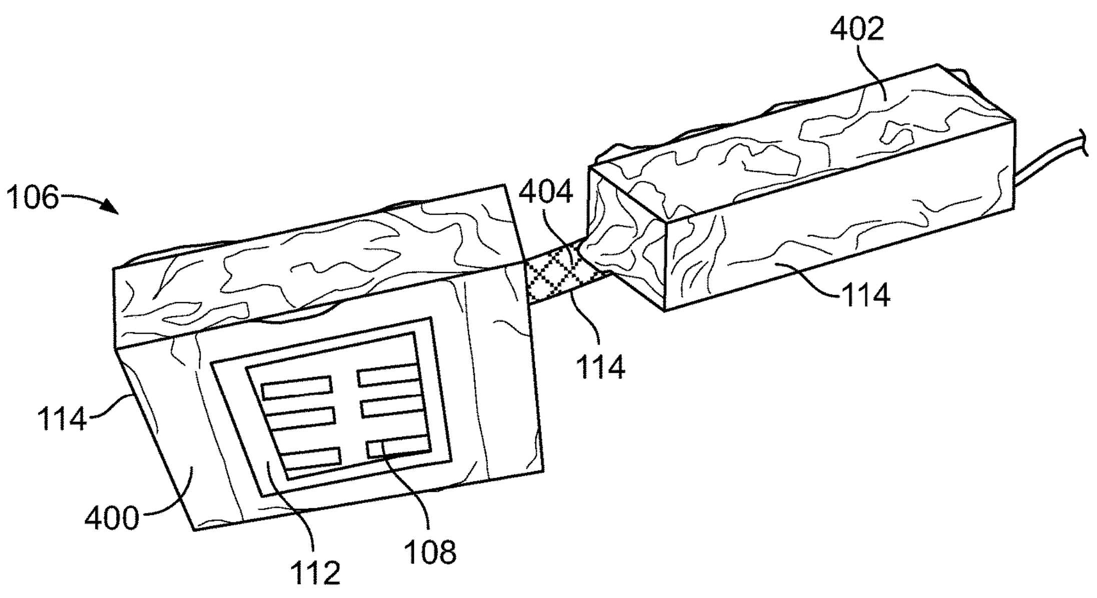
FIG. 27 illustrates a perspective view of a module, according to an embodiment of the present disclosure.

FIG. 27 illustrates a perspective view of a module 106, according to an embodiment of the present disclosure. The module 106 includes a sub-housing 400 retaining one or more UV light emitters 108. The sub-housing 400 is coupled to a power supply 402 through a cable 404. In contrast to the embodiments shown in FIGS. 4-6, the sub-housing 400 and the power supply 402 may not be secured within a common bracket. Optionally, the sub-housing 400 and the power supply 402 may be secured to a bracket, such as the bracket 150 shown and described with respect to FIGS. 4-6, for example.

An EMI shield 114 (for example, a first EMI shield) is disposed around portions of the sub-housing 400. In at least one embodiment, the EMI shield 114 is disposed around all portions of the sub-housing 400, except the aperture 112. As an example, the EMI shield 114 is a metal foil (for example, a stainless steel, aluminum, or the like foil) that extends around portions of the sub-housing 400. The EMI shield 114 blocks, attenuates, or otherwise hinders EMI that may be generated by operation of the UV light emitters 108 from passing therethrough (and/or blocks EMI from passing into the sub-housing 400).

The EMI shield 114 (for example, a second EMI shield) may also extend around portions of the power supply 402 and/or the cable 404. For example, the EMI shield 114 may wrap around all portions of the power supply 402 and/or the cable 404. In at least one embodiment, the EMI shield 114 covers an entirety of the module 106 including the sub-housing 400, the power supply 402, and the cable 404, except for the aperture 112. The EMI shield 114 blocks, attenuates, or otherwise hinders EMI from passing between the sub-housing 400 and the power supply 402.

Further, by separating the sub-housing 400 from the power supply 402 (and connecting via the cable 404), the module 106 may be more readily integrated and used in certain confined areas in which a common housing retaining both may be too large. The sub-housing 400 as shown in FIG. 27 has a low profile and may fit into smaller spaces.

The EMI shield 114 may be used with any of the embodiments described herein. Further, a module including the sub-housing 400 separated from the power supply 402 (as shown in FIG. 27) may be used with any of the embodiments described herein, whether with the EMI shield 114 or without the EMI shield 114.

Figure 28:
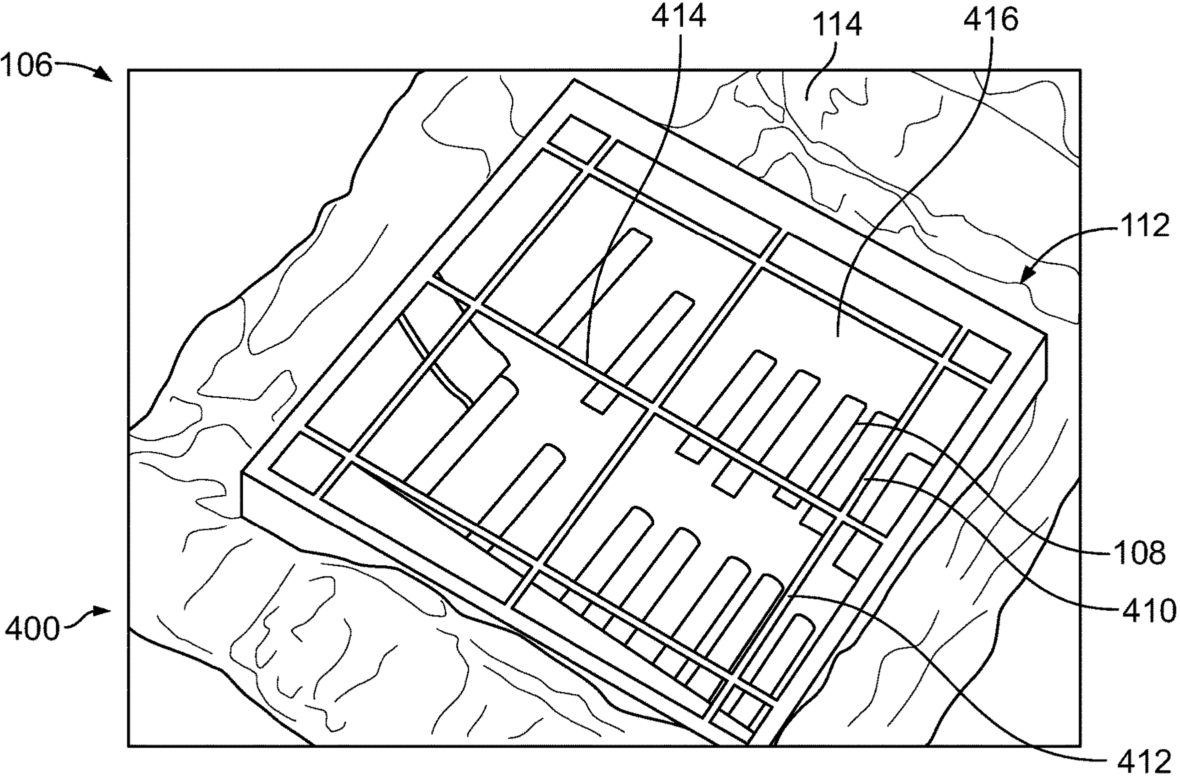
FIG. 28 illustrates a perspective bottom view of a sub-housing of the module of FIG. 27.

FIG. 28 illustrates a perspective bottom view of the sub-housing 400 of the module 106 of FIG. 27. In at least one embodiment, an EMI grid 410 is disposed within the aperture 112. The EMI grid 410 includes a plurality of longitudinal beams 412 that intersect a plurality of lateral beams 414, defining passages 416 therebetween. The beams 412 and 414 may have a thickness between 0.001"-0.010", for example. In this manner, the EMI grid 410 can be a mesh screen or cage, for example. The EMI grid 410 also hinders passage of EMI into or out of the module 106. In at least one embodiment, the EMI grid 410 can be formed of stainless steel. Alternatively, the module 106 does not include the EMI grid 410.

Figure 29:
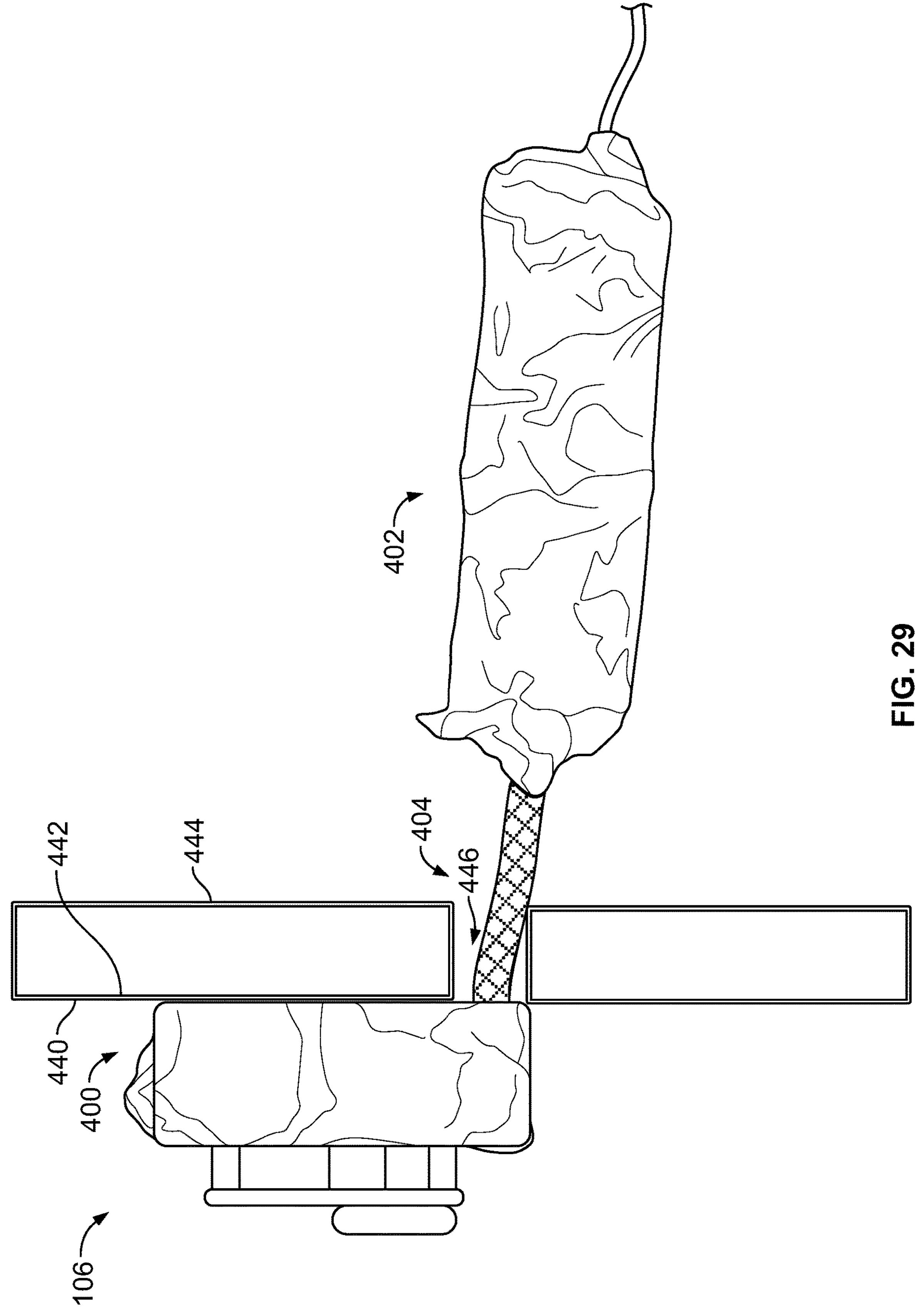
FIG. 29 illustrates a lateral view of the module of FIG. 27 secured to a wall, according to an embodiment of the present disclosure.

FIG. 29 illustrates a lateral view of the module 106 of FIG. 27 secured to a wall 440, according to an embodiment of the present disclosure. The sub-housing 400 can be mounted on a first surface 442 (such as an outer or inner surface) of the wall 440, and the power supply 402 can be disposed behind the wall 440. For example, the power supply 402 can be secured behind a second surface 444 (opposite from the first surface) of the wall 440. An opening 446 formed through the wall 440 is configured to allow the cable 404 to pass therethrough. In this manner, the wall 440 also isolates the sub-housing 400 from the power supply 402.

The wall 440 may be a portion of a room. For example, the wall 440 may be a wall of a lavatory, such as the lavatory 220 shown in FIGS. 18, 19, 23, and 24.

Figures 30, 31, 32:
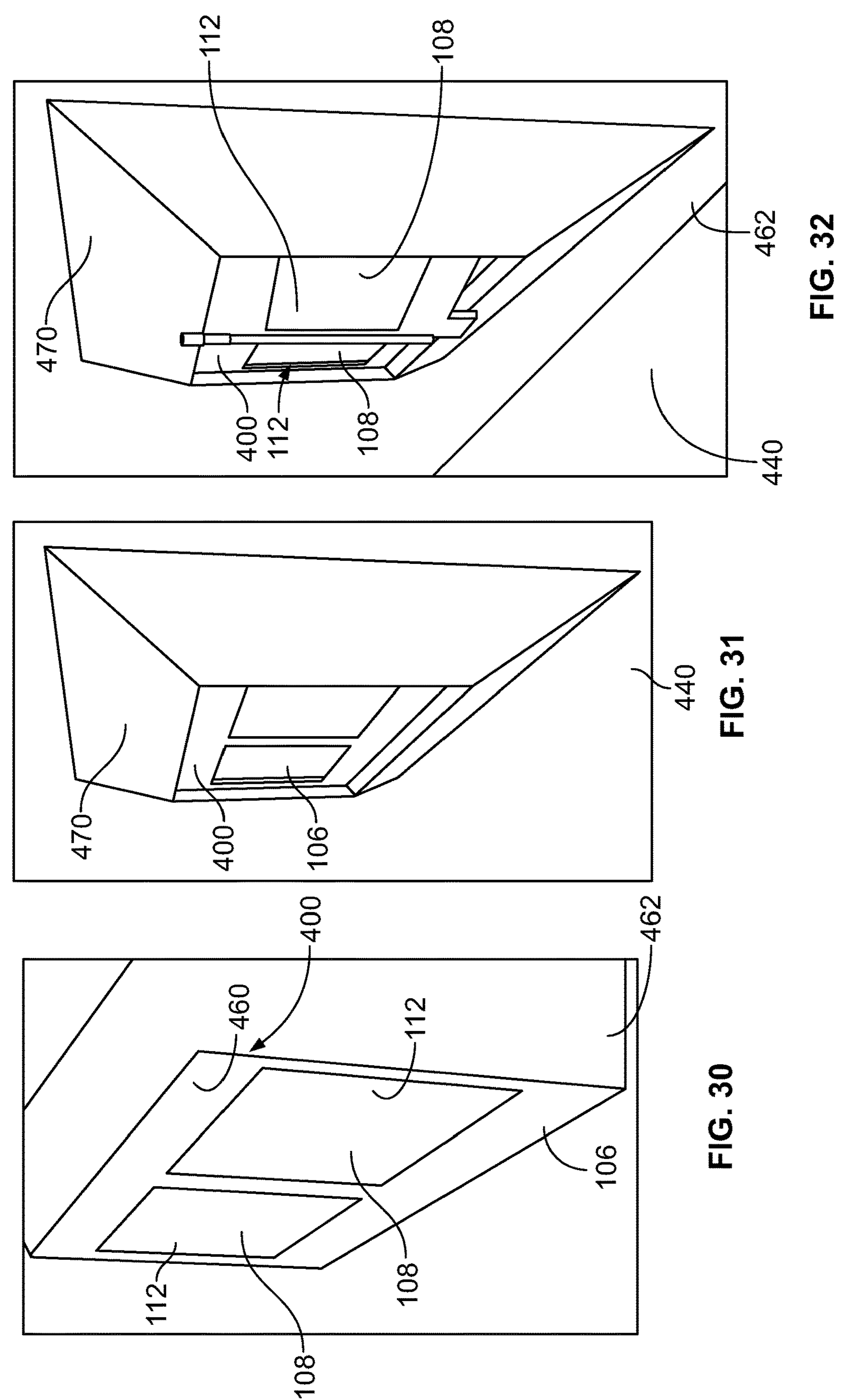
FIG. 30 illustrates a perspective front, lateral view of a module secured to a wall, according to an embodiment of the present disclosure.
FIG. 31 illustrates a perspective front, lateral view of a module secured to a wall, according to an embodiment of the present disclosure.
FIG. 32 illustrates a perspective front, lateral view of a module secured to a wall, according to an embodiment of the present disclosure.

FIG. 30 illustrates a perspective front, lateral view of the module 106 secured to the wall 440, according to an embodiment of the present disclosure. The sub-housing 400 may be secured to the wall 440 such that a front face 460, including the apertures 112, is flush with a front surface 462 of the wall 440.

FIG. 31 illustrates a perspective front, lateral view of the module 106 secured to the wall 440, according to an embodiment of the present disclosure. In this embodiment, the sub-housing 400 can be secured within a surrounding collar 470 that mounts the sub-housing 400 to the wall 440.

FIG. 32 illustrates a perspective front, lateral view of the module 106 secured to the wall 440, according to an embodiment of the present disclosure. This embodiment is similar to that shown in FIG. 31, except that the apertures 112 may be angled (that is, not parallel) to the front surface 462 of the wall 440.

Figure 33:
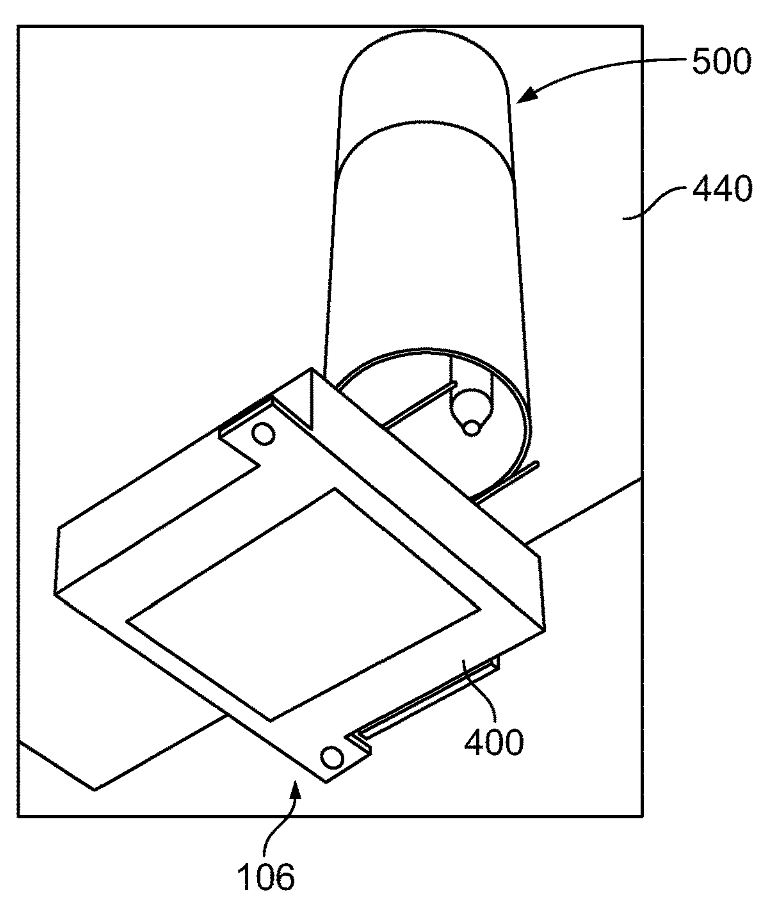
FIG. 33 illustrates a perspective front view of a module secured to a wall, according to an embodiment of the present disclosure.

FIG. 33 illustrates a perspective front view of the module 106 secured to the wall 440, according to an embodiment of the present disclosure. In this embodiment, a shielding shroud 500, such as a metal cylinder, is secured to and/or behind the wall 440. The power supply 402 (shown in FIG. 29, for example) is retained within the shielding shroud 500. In this embodiment, the shielding shroud 500 provides the EMI shielding for the power supply 402. Additional EMI shielding, such as in the form of a metal foil, may nor may not extend around the power supply 402 within the shielding shroud 500.

In at least one embodiment, the shielding shroud 500 is configured to fit into and be retained within an opening formed in the wall 440. As such, the shielding shroud 500 can be easily installed into the wall 440.

Figure 34:
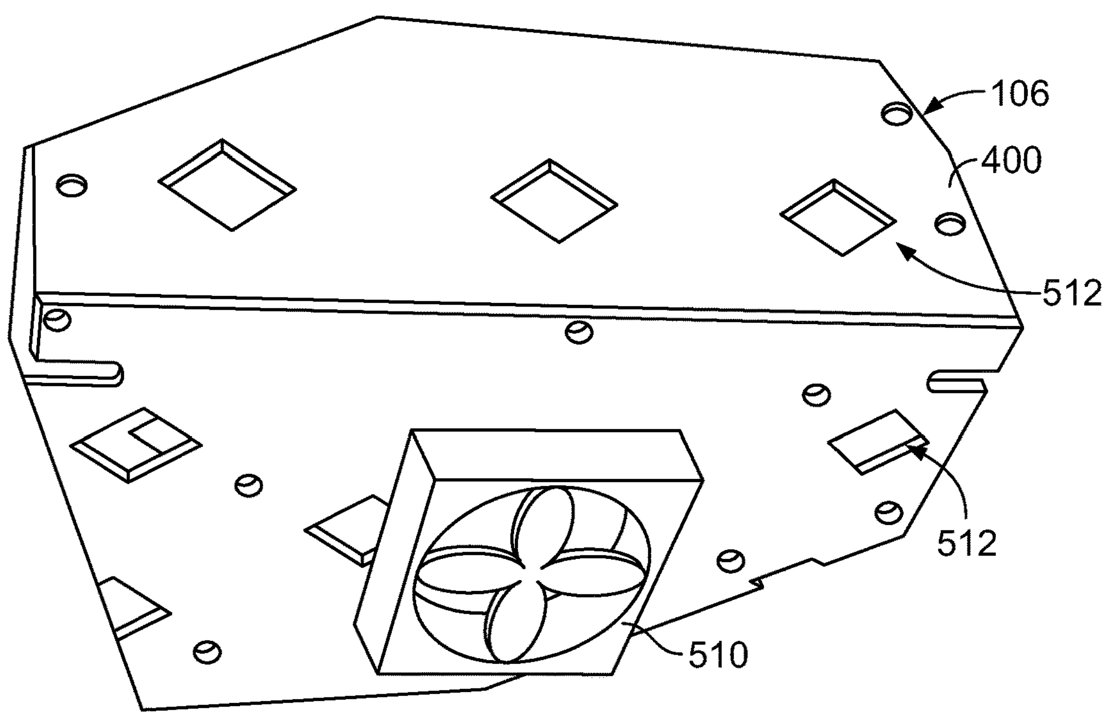
FIG. 34 illustrates a perspective rear view of a sub-housing of a module, according to an embodiment of the present disclosure.

FIG. 34 illustrates a perspective rear view of the sub-housing 400 of the module 106, according to an embodiment of the present disclosure. As shown, the sub-housing 400 may include a cooling fan 510 and a plurality of ventilation openings 512. The cooling fan 510 operates to cool the UV light emitters 108 during operation, and the ventilation openings 512 draw in cooling air and/or allow air within the sub-housing 400 to pass therethrough. The cooling fan 510 and the ventilation openings 512 may be used with any of the embodiments described herein. In embodiments in which an EMI shield covers portions of the sub-housing 400, the EMI shield does not cover the cooling fan 510 and the ventilation openings 512.

The ventilation openings 512 can be sized and shaped depending on EMI wavelength requirements. For example, in at least one embodiment, the ventilation openings 512 can be between 0.5"-1.0".

Figure 35:
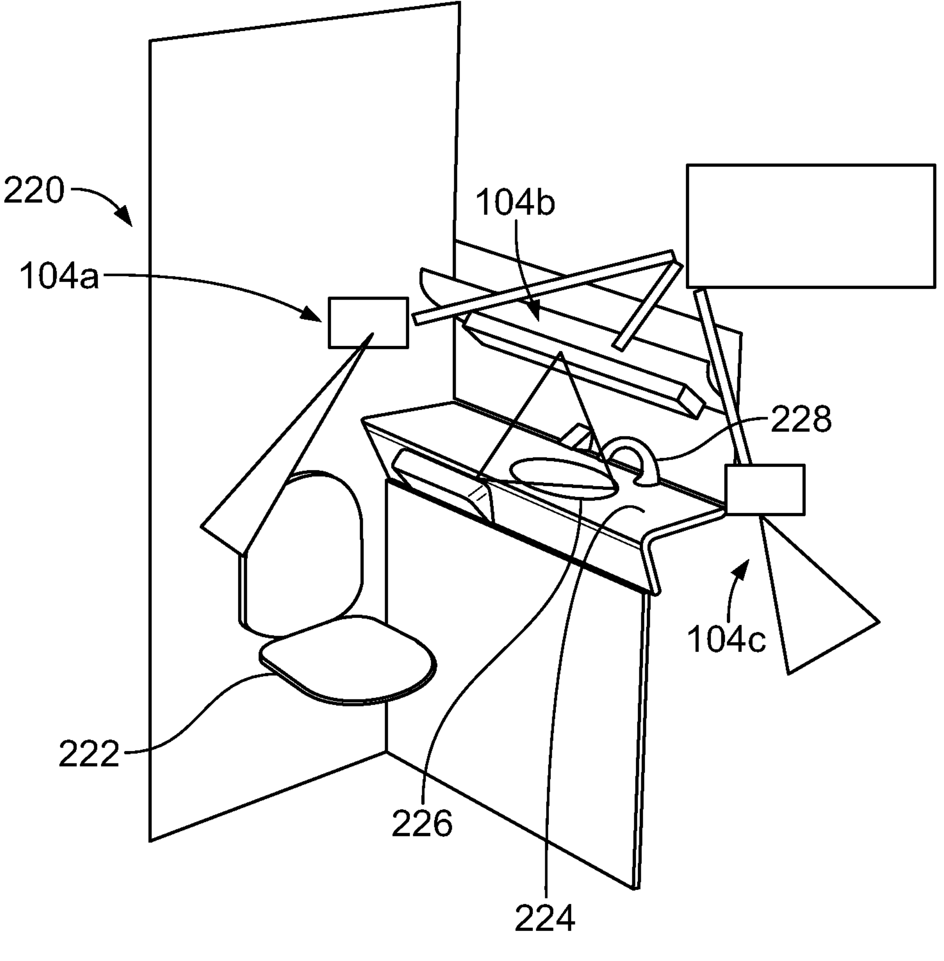
FIG. 35 illustrates a perspective internal view of a lavatory, according to an embodiment of the present disclosure.

FIG. 35 illustrates a perspective internal view of the lavatory 220, according to an embodiment of the present disclosure. The lavatory 220 can include a plurality of UV lamps, according to any of the embodiments described herein. For example, a first UV lamp **104*a* is configured to emit UV light onto a flush handle of the toilet 222. A second UV lamp 104*b* is configured to emit UV light onto the counter 224, including the sink 226 and the faucet 228. A third UV lamp 104*c* is configured to emit UV light onto a door handle, for example. The lavatory 220** can include more or less UV lamps than shown.

Figure 36:
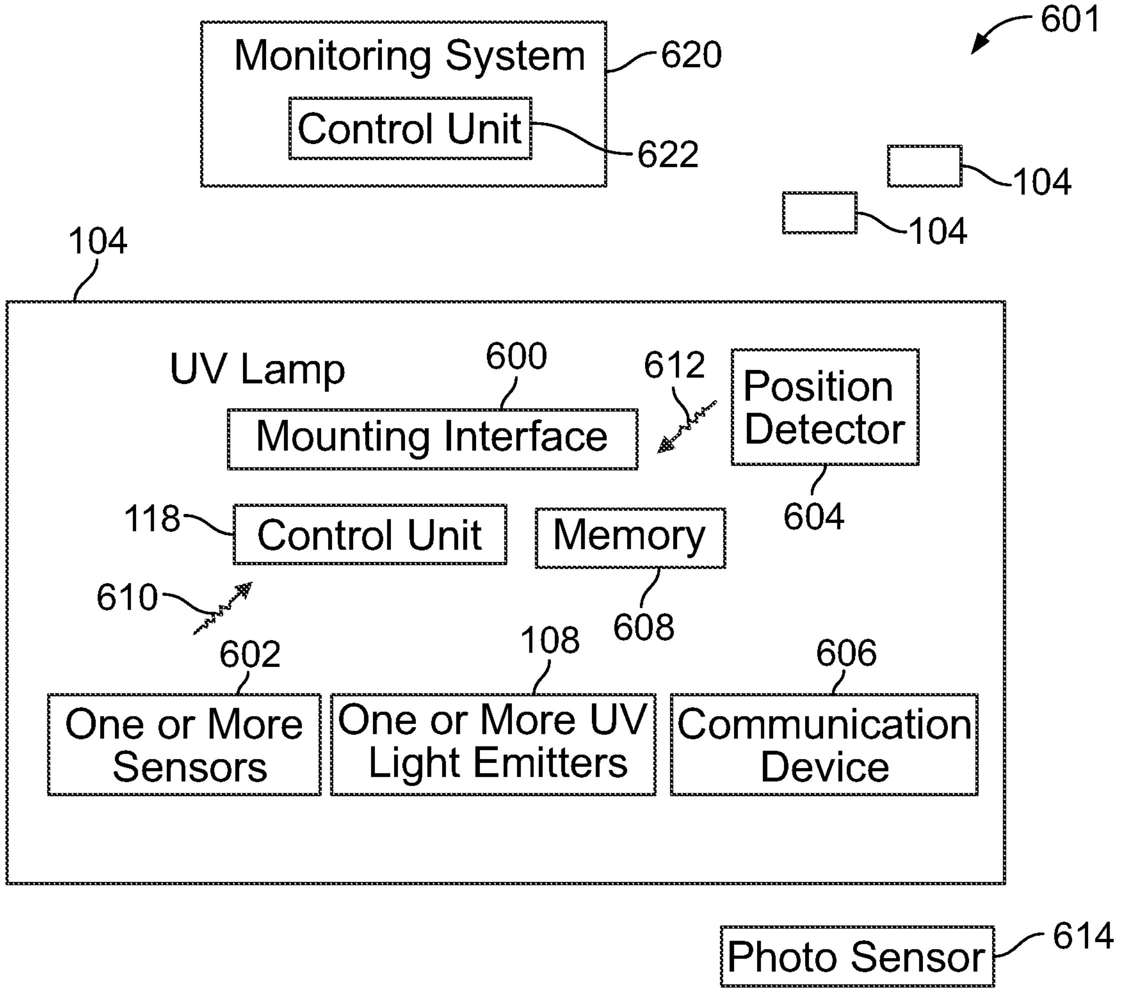
FIG. 36 illustrates a schematic block diagram of a UV lamp, according to an embodiment of the present disclosure.

FIG. 36 illustrates a schematic block diagram of a UV lamp 104, according to an embodiment of the present disclosure. The UV lamp 104 can be configured as any of the UV lamps 104 shown and described with respect to FIGS. 1-35. For example, the UV lamp 104 can include one or more modules 106, such as shown in FIG. 1. As another example, the UV lamp 104 can be a single assembly that does not include a plurality of modules coupled together. The UV lamp 104 includes one or more UV light emitters 108, whether in a module or not.

As described herein, the UV lamp 104 includes a mounting interface 600 removably securable to a securing mount. That is, the mounting interface is configured to be selectively secured to and removed from one or more securing mounts within an area, such as within an aircraft. The mounting interface 600 allows the UV lamp 104 to be quickly secured to and removed from a securing mount, and secured to a different securing mount. A plurality of securing mounts having a common securing interface that allows the mounting interfaces 600 of UV lamps 104 to connect and disconnect thereto. The UV lamp 104 can be interchanged in relation to a plurality of securing mounts located within an area, such as within an aircraft. As such, the UV lamp 104 is a portable device that can be secured to and removed from various locations within an area. In at least one embodiment, a system 601 for disinfecting one or more components within an area includes a plurality of UV lamps 104 in communication with a monitoring system 620.

The UV lamp 104 is a portable assembly that can be securely mounted at various locations within the area, such as within a vehicle. The UV lamp 104 includes the mounting interface 600 that is configured to allow the UV lamp 104 to be selectively secured to and removed from a reciprocal securing mount. For example, the mounting interface 600 can include one or more latches, clasps, plugs, sockets, an interference fitting structure, and/or the like that are configured to removably couple to reciprocal features of the securing mount. As an example, the mounting interface 600 can include a flange, collar, or the like that is configured to be plugged into a reciprocal socket or the like of the securing mount, or vice versa. In this manner, the UV lamp 104 can be selectively positioned and removed from various locations within the area. The securing mount can be secured to a particular location through fasteners, adhesives, and/or the like. In at least one embodiment, a plurality of securing mounts are located throughout an area, such as the internal cabin of the vehicle.

In at least one embodiment, the UV lamp 104 includes a control unit 118 that is in communication with the one or more UV light emitters 108, one or more sensors 602, a position detector 604, and a communication device 606, such as through one or more wired or wireless connections. The control unit 118 is also coupled to a memory 608. In at least one embodiment, the control unit 118 includes the memory 608. In at least one other embodiment, the control unit 118 can be remotely located from the UV lamp 104, such as within a monitoring sub-system (for example, a computing device such as a handheld smart phone or smart table, a laptop computer, a computer workstation, and/or the like) that is in communication with the UV lamp 104.

Optionally, a UV lamp 104 that is permanently secured to a location can include the sensors 602, a position detector 604, and the communication device 606, for example. That is, in certain embodiments, the UV lamp 104 may or may not be removably securable to a securing mount. Such UV lamps 104 may be configured to communicate with other UV lamps 104, with an external management system, and be controlled as described with respect to FIGS. 36-41 whether or not they are interchangeable, removably securable, or permanently fixed in position.

The control unit 118 is configured to control operation of the one or more UV light emitters 108 to disinfect a component, as described herein.

The control unit 118 is in communication with the one or more sensors and is configured to receive presence signals 610 from the one or more sensors, such as presence sensors. The presence signals 610 indicate presence of and/or movement of individuals, objects, and/or the like that are proximate to the UV lamp 104, such as within a UV disinfection range of the one or more UV light emitters 108. In at least one embodiment, the sensor(s) 602 include an infrared sensor, an ultrasonic sensor, a camera, a proximity sensor, and/or the like.

The control unit 118 is in communication with the position detector 604 and is configured to receive position signals from the position detector 604. The position signals indicate the position of the UV lamp 104 within an area, such as an internal cabin of a vehicle. In at least one embodiment, the position detector can be a radio frequency identification (RFID) chip, a global positioning system (GPS) device, a localized positioning system device that is configured to detect a location via triangulation, an electromagnetic detector in communication with an electromagnetic generator, and/or the like.

The control unit 118 is in communication with the communication device 606 and is configured to communicate with various other devices through the communication device 606. For example, the communication device 606 can be one or more antennas, a transceiver, a Bluetooth device, a WiFI device, and/or the like.

The UV lamp 104 provides a fully self-contained, portable, and universal UV system. The UV lamp 104 can be mounted or retrofitted to any area, such as inside of vehicle, via the mounting interface 600. For example, the UV lamp 104 can be selectively secured to and removed from a reciprocal securing mount within a flight deck, crew rest area, galley, main cabin, lavatory, cargo area, assembly areas, and other areas within an internal cabin of an aircraft.

In operation, the control unit 118 receives presence signals 610 from the one or more sensors 602. The control unit 118 determines presence of individuals proximate to the UV lamp 104 (such as within the disinfection range of the one or more UV light emitters 108). In at least one embodiment, based on the frequency of movement within the area proximate to the UV lamp 104, the control unit 118 controls a power level, an irradiance level, intensity level, and/or the like of the one or more UV light emitters 108. For example, based on occupancy in the area of luminance of the UV light emitters 108, as detected from the presence signals 610 received from the one or more sensors 602, the control unit 118 controls the power level of the UV light. As such, the battery power of the UV lamp 104 is preserved, and generated ozone can be limited, as the control unit 118 can modulate the power level of the one or more UV light emitters 108 if the area proximate to the UV lamp 104 is not frequently occupied by individuals. That is, the less the area proximate to the UV lamp 104 is occupied by individuals, the control unit 118 can reduce the power level of the UV light emitters 108 during a disinfection cycle (such as when no individuals are present). Conversely, the more the area proximate to the UV lamp 104 is occupied by individuals, the control unit 118 can increase the power level of the UV light emitters 108 during the disinfection cycle.

The control unit 118 can store presence data, determined from the presence signals 610, in the memory 608. The control unit 118 can analyze the presence data to determine the frequency of movement (for example, occupancy by individuals) over time (for example, a week, a month, a year, or more). In this manner, the control unit 118 can be a smart unit that learns from past behaviors of human activity in an area (and other factors such as a flight route, passenger load, and/or the like), and predict when a certain amount of UV light as emitted by the one or more UV light emitters 108 will be needed. As such, the control unit 118 can predict future operation of the UV light emitters 108 based on the presence data, such as may be stored in the memory 608. Therefore, the control unit 118 can adjust irradiance values and times for optimal disinfection and safety based on the presence data stored in the memory 608.

Additionally, the control unit 118 receives one or more position signals 612 from the position detector 604. The position signals 612 are indicative of the a location of the UV lamp 104 within an area, such as an internal cabin of a vehicle. The position signals 612 allow the control unit 118 to determine the location of the UV lamp 104 within the area. For example, the control unit 118, through the position signals 612 received from the position detector 604, determines the location of the UV lamp 104 within the area, and control the power, irradiance level, and time of UV light emission output by the one or more UV light emitters 108 based on the determined location of the UV lamp 104. For example, when the UV lamp 104 is within a lavatory, the control unit 118 may operate the one or more UV light emitters 108 at a first power for a first time period. When the UV lamp 104 is within a different area, such as a cargo area, galley, flight deck, or the like that may not require the same amount of disinfection, the control unit 118 may operate the UV light emitters 108 at a second power, which may be less than the first power, for a second time period, which may be less than the first time period.

As an example, any number of UV lamps 104 may be installed at various locations in an area, such as within an internal cabin of an aircraft. The position detectors 604 detect the locations of the UV lamps 104, and output the position signals 612 to the control units 118, thereby allowing the control units 118 of the respective UV lamps 104 to determine the locations of the UV lamps 104 within the area. The control unit 118 of each UV lamp 104 can analyze mapping data, such as stored in the memory 608 and/or another memory in communication with the control unit 118, to apply logical or physical mapping to determine the environment of the UV lamp 104 within the area (such as within a lavatory, a galley, flight deck, crew rest, passenger row, and/or the like). According to the detected location of the UV lamp, the control unit 118 is programmed (such as via data stored in the memory 608) to control the one or more UV light emitters 108 to emit UV light at a particular irradiance and/or time period. Control parameters (such as power, irradiance level, time period, and the like) stored in the memory 608 for the one or more UV light emitters 108 within a location can be based on a type of surface material to treat, amount of area and/air to disinfect, time intervals of use based on known or predicted occupancy uses, and/or the like.). As such, the control unit 118 can dynamically control the one or more UV light emitters 108 based on a detected location of the UV lamp 104.

In another example, such as when the position detector 604 is an RFID reader, chip, or the like, once the UV lamp 104 is coupled to a particular securing mount within an area, the control unit 118 can determine the location of the UV lamp 104, and therefore control the UV lamp 104 accordingly, as described above. Such information can be shared between UV lamps 104 and an external monitoring system for power management of the UV lamps 104, particularly in cases where the UV lamps 104 are drawing from aircraft power (and/or when battery power is low).

In an example, the UV lamp 104 can include UV light emitters 108 that are configured to emit UV light at different wavelengths (for example, 222 nm, 254 nm, and the like). The control unit 118 can operate the different UV light emitters 108 based on a detected location of the UV lamp 104, as detected by the position detector 604, and/or the presence and/or frequency of individuals within the location of the UV lamp 104, as detected by the one or more sensor 602. For example, UV light at different wavelengths can be emitted from the one or more UV light emitters 108 based on sensed and/or predicted behavior within the location of the UV lamp 104. For example, the control unit 118 may operate the UV light emitters 108 to emit UV light at a first wavelength, such as 254 nm, when no individuals are present at the location, and a second wavelength, such as 222 nm, if an individual is present at the location The selective control of different UV light emitters 108 can also be based on the particular location of that UV lamp 104 within an area.

In at least one embodiment, the UV lamp 104 can have scalable and/or programmable power control to account for future pathogens, different or new light emitters, applications, locations, and/or the like. For instance, in a certain mode (222 nm, 254 nm, or the like that can be reduced with a certain waveform), and when in the presence of individuals, the control unit 118 can switch to another mode such as 222 nm based on the sensed and/or known parameters of human occupancy. As such, the power supply could be controlled accordingly, as the control unit 118 can selectively control a power level, such as by reducing a power level at certain times during use with different light emitters 108.

In one example, a feedback loop can be used to determine the direction and power of irradiance, and the control unit 118 can control the power supply accordingly. Such is useful when the UV lamp 104 includes an optional secondary power supply (such as a battery or USB power), because the power output of the one or more UV light emitters 108 may vary. For example, in a scenario in which the UV lamp 104 has an input voltage of 120 V from a battery, but the UV lamp 104 is also capable of providing AC input voltage of 170 V, the control unit 118 can control the power supply output by adjusting a duty cycle and frequency sensed to the one or more UV light emitters 108. In this case, the output of the light emitters 108 can be sensed (for example, via a photo sensor 614 in communication with the control unit 118), and the control unit 118 can adjust the power supply accordingly. The photo sensor 614 can be on and/or within the UV lamp 104, or mounted elsewhere within the area. Thus, the control unit 118 can change the dosage time, and/or the signal to the bulb, based on the sensed output voltage.

In at least one embodiment, the communication device 606 of the UV lamp 104 can be utilized to communicate data with other UV lamps 104, such as within an internal cabin of an aircraft, and/or with an external system that receives data for processing for a number of reasons, such as providing information to crew, airline, maintenance, etc. regarding health, battery power, sensed behavior of occupants, determine which unit has certain battery level for swapping based on location, use, sensed or known human behavior, power level, etc. Thus, on a system level, an external monitoring system 620 can provide information as how to correct potential issues with UV lamps 104, and possible issues with total ozone potentially created by UV lamps 104. The external monitoring system 620 can then control certain UV lamps 104 based on a variety of factors (for example, ozone, behavior, etc.). A user may have the option to set a certain threshold for each UV lamp 104 based on the data generated and processed from all or some of the UV lamps 104 in real time. Use of UV lamps 104 within an internal cabin of an aircraft, can be optimized for a given aircraft or fleet, and the route requirements for that particular aircraft (for example, and seasonal use, passenger capacity, and the like). As such, a control unit 622 of the monitoring system 620 can sense data, aggregate the data, and learn from the data to control the UV lamps 104.

In at least one embodiment, the UV lamp 104 can be mounted dynamically within an area, such as an internal cabin of an aircraft, such as to a moveable and/or robotic arm, such as in a flight device of an aircraft. As another example, a charging and/or data cart (or other external system) that can be used to dock and charge the UV lamps 104 during flight, turn time, etc. to download and/or upload data with respect to the UV lamps 104, which further allows for scalability or reprogramming of the UV modules based on changing behaviors, needs, etc. that may have been learned by one or more UV lamps 104 during use. A UV lamp 104 can also be used, in conjunction with a camera, to identify damage or foreign object debris at a location. to monitor a condition over time, and/or to fix issues in flight like low commodities, soap, for cleaning, and/or the like.

In at least one embodiment, the UV lamp 104 includes an internal power source (such as a battery, capacitor(s), or the like), which can be replaced or recharged. For example, the UV lamp 104 can be plugged into USB power, and recharged on a continuous basis. During a sanitizing cycle, when power is needed, the UV lamp 104 can be configured to use both the battery and the USB power. Alternatively, the UV lamp 104 can be infrequently powered from a USB/120 V source, in conjunction with the battery power, for a particular duty cycle.

Figure 37:
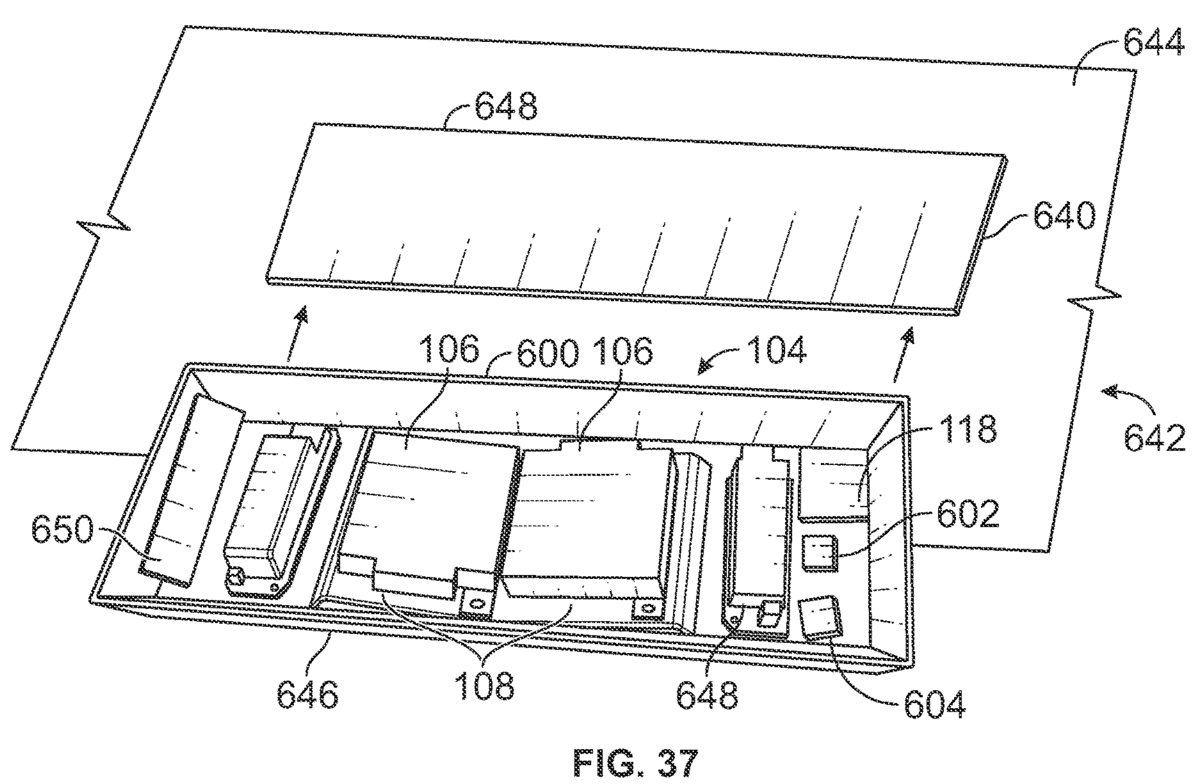
FIG. 37 illustrates a perspective rear view of a UV lamp separated from a securing mount within an area, according to an embodiment of the present disclosure.
Figure 38:
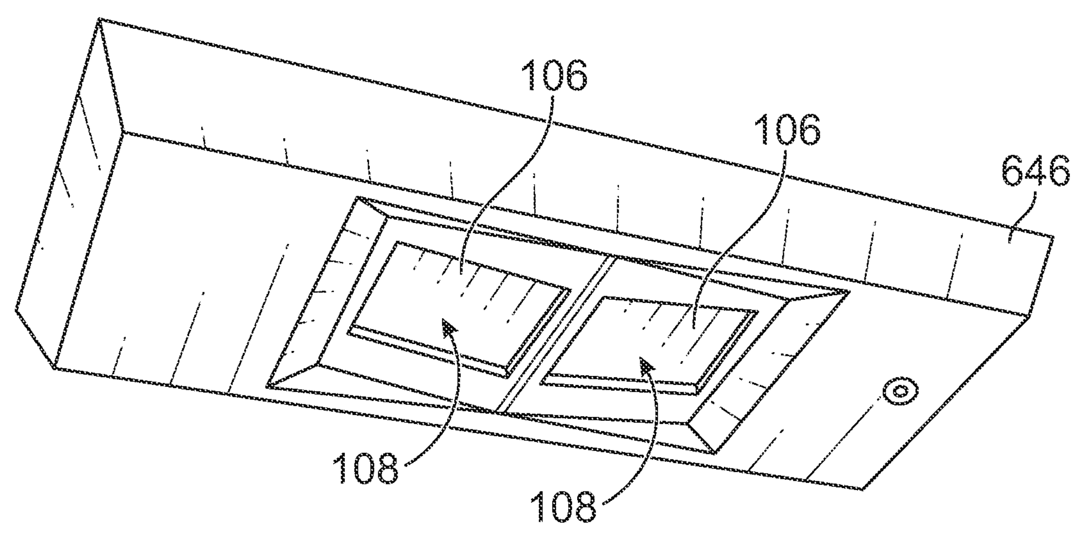
FIG. 38 illustrates a perspective front view of the UV lamp of FIG. 37.

FIG. 37 illustrates a perspective rear view of the UV lamp 104 separated from a securing mount 640 within an area 642, according to an embodiment of the present disclosure. FIG. 38 illustrates a perspective front view of the UV lamp 104.

Referring to FIGS. 37 and 38, the area 642 may be an internal cabin of an aircraft. The securing mount 640 is secured to a surface 644, such as a wall, ceiling, floor, or the like.

The UV lamp 104 includes a housing 646 that includes the mounting interface 600. The mounting interface 600 is configured to removably secure to a reciprocal mounting interface 648 of the securing mount 640. For example, the mounting interface 600 can be configured to snapably, latchably, or otherwise removably secure to the mounting interface 648.

In at least one embodiment, the housing 646 retains a power supply 648, such as an input to a main power supply within a vehicle. The housing 646 can also retain a secondary power supply 650, such as one or more batteries that are separate and distinct from the power supply 648, a USB port, and/or the like. In at least one embodiment, UV light emitters 108 are disposed within a plurality of modules 106.

The control unit 118 is also retained by the housing 646. The sensor 602 and the position detector 604 are also retained by the housing 646.

Figure 39:
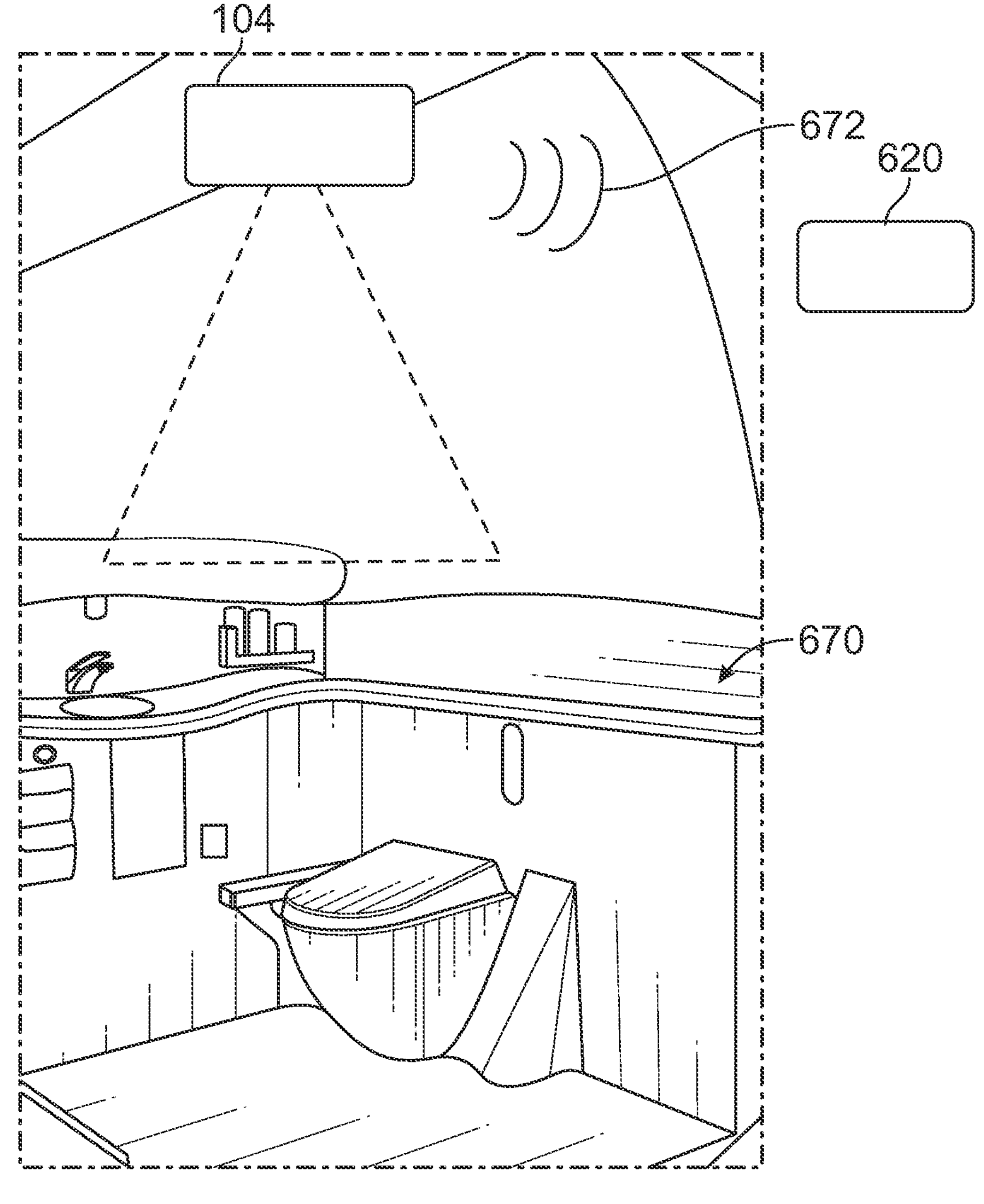
FIG. 39 illustrates a perspective view of a UV lamp within a lavatory, according to an embodiment of the present disclosure.

FIG. 39 illustrates a perspective view of a UV lamp 104 within a lavatory 670, according to an embodiment of the present disclosure. As described above, the UV lamp 104 can be in communication with a monitoring system 620 (remote from the UV lamp 104), such as an aircraft management system. The UV lamp 104 is configured to output one or more location signals 672 to the monitoring system 620. The location signal(s) 672 are received by the monitoring system 620, which determines the location of the UV lamp 104 based on the location signal(s) 672. The monitoring system 620 can operate the UV lamp 104 based on a detected location of the UV lamp 104, as described above.

Figure 40:
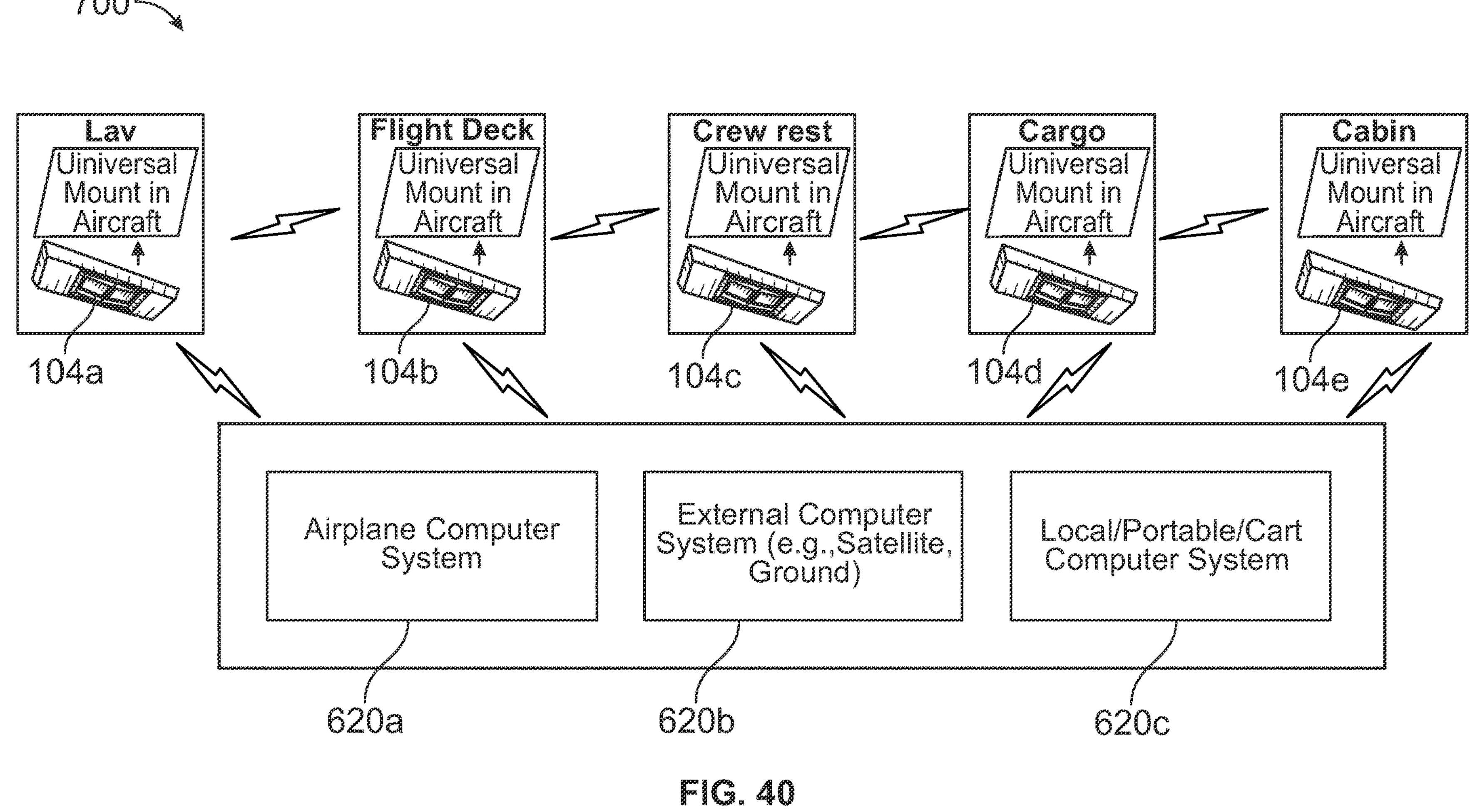
FIG. 40 illustrates a system for controlling a plurality of UV lamps within an area, according to an embodiment of the present disclosure.

FIG. 40 illustrates a system for controlling a plurality of UV lamps 104*a*, 104*b*, 104*c*, 104*d*, and 104*e* within an area 700, according to an embodiment of the present disclosure. In at least one embodiment, the area 700 is within an aircraft. The UV lamp 104*a* is in a lavatory of the aircraft. The UV lamp 104*b* is in a flight deck of the aircraft. The UV lamp 104*c* is in a crew rest area of the aircraft. The UV lamp 104*d* is in a cargo area of the aircraft. The UV lamp 104*e* is in a passenger cabin of the aircraft.

The UV lamps 104*a-e* are able to communicate with one another, such as through respective communication devices, as well as external systems, such as an airplane computer system 620*a*, an external computer system 620*b*, a local cart computer system 620*c*, and/or the like.

The UV lamps 104*a-e* are able to detect their locations within the area 700, as described above. The UV lamps 104*a-e* are further configured to predict disinfection requirements for their respective locations, based on their locations, frequency of movement within the areas, and/or the like, as described above. The UV lamps 104*a-e* can communicate with each other, and the with external systems 620*a-c*, in order to provide information regarding power usage, data transfer, functionality, scalability, and/or the like.

Figure 41:
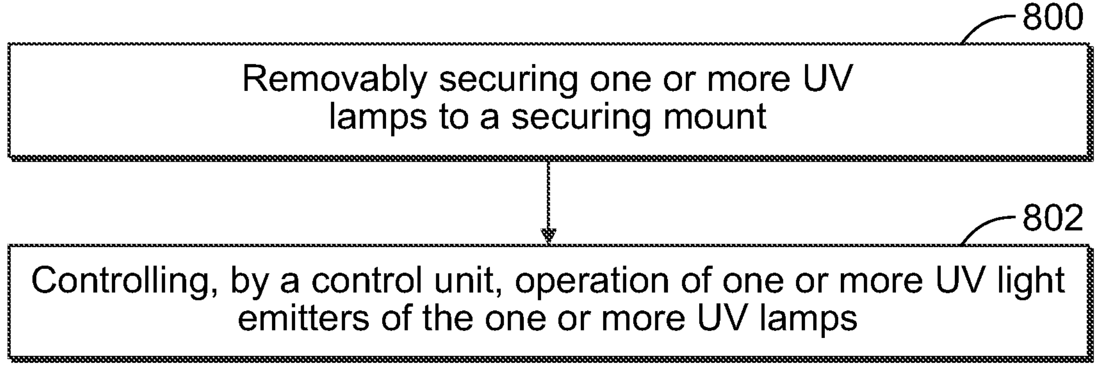
FIG. 41 is a flow chart of a method for disinfecting one or more components, according to an embodiment of the present disclosure.

FIG. 41 illustrates a flow chart of a method for disinfecting one or more components, according to an embodiment of the present disclosure. The method includes, at 800, removably securing one or more ultraviolet (UV) lamps including one or more UV light emitters configured to emit UV light to a securing mount.

In at least one embodiment, the method also includes, at 802, controlling, by a control unit, operation of the one or more UV light emitters. As a further example, the method also includes disposing the control within the one or more UV lamps.

In at least one example, the method includes communicatively coupling one or more sensors of the one or more UV lamps with the control unit; and detecting, by the one or more sensors, presence or movement proximate to the one or more UV lamps. As a further example, the method includes controlling, by the control unit, one or more of a power level, an irradiance level, an intensity level, or a timing period for disinfection of the one or more UV lamps based on presence signals received from the one or more sensors. As another example, the method includes predicting, by the control unit, future operation of the one or more UV light emitters based on presence data stored in a memory.

In at least one example, the method includes communicatively coupling a position detector of the one or more UV lamps with the control unit; and detecting, by the position detector, a location of the one or more UV lamps within an area. As a further example, the method include operating, by the control unit, the one or more UV light emitters based on the location of the UV lamp, as detected by the position detector, within the area.

In at least one embodiment, the method includes emitting, by first UV light emitters, the UV light at a first wavelength; and emitting, by second UV light emitters, the UV light at a second wavelength that differs from the first wavelength. As an example, the method includes controlling, by the control unit, the one or more UV light emitters to emit the UV light at different wavelengths based on sensed or predicted behavior proximate to the UV lamp.

In at least one embodiment, the method includes providing the one or more UV lamps with a power supply, and one or more batteries.

In at least one example, the method includes operating, by the control unit, the one or more UV light emitters based on a sensed output voltage.

In at least one embodiment, the method includes communicating between a plurality of UV lamps.

In at least one example, the method includes communicatively coupling an external monitoring system with the one or more UV lamps; and controlling, by the external monitoring system, the one or more UV lamps.

Figure 42:
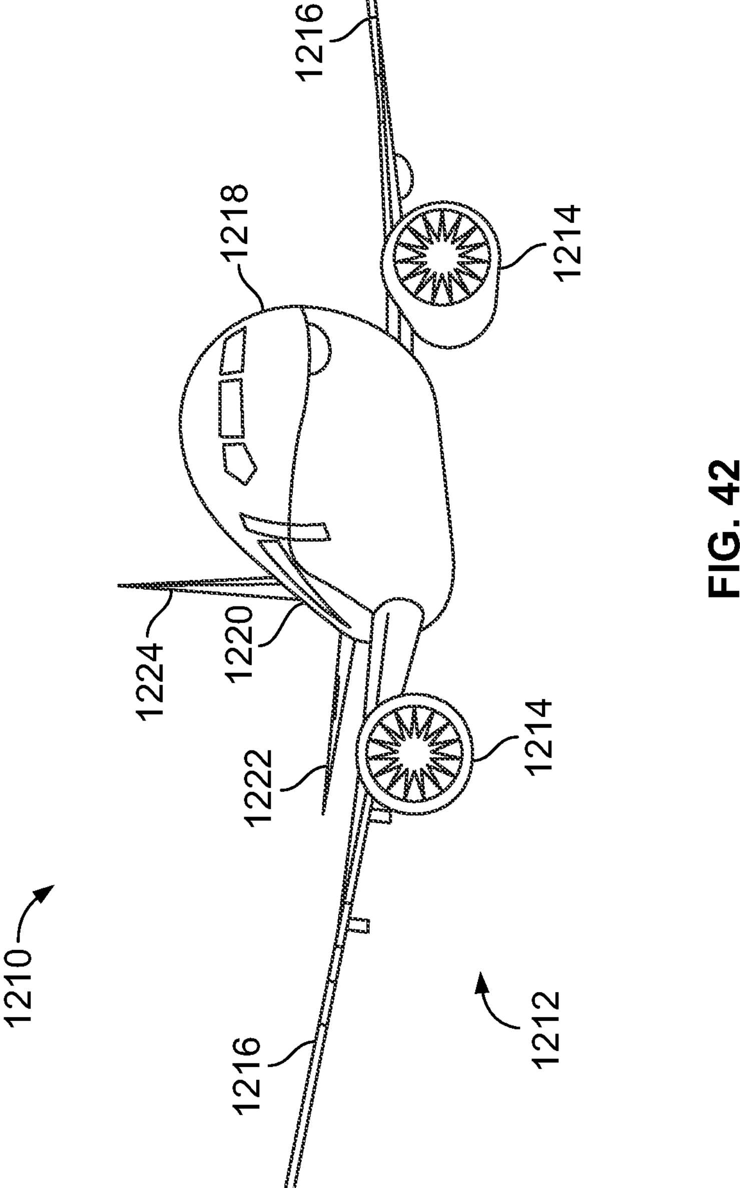
FIG. 42 illustrates a perspective front view of an aircraft, according to an embodiment of the present disclosure.

FIG. 42 illustrates a perspective front view of an aircraft 1210, according to an embodiment of the present disclosure. The aircraft 1210 includes a propulsion system 1212 that includes engines 1214, for example. Optionally, the propulsion system 1212 may include more engines 1214 than shown. The engines 1214 are carried by wings 1216 of the aircraft 1210. In other embodiments, the engines 1214 may be carried by a fuselage 1218 and/or an empennage 1220. The empennage 1220 may also support horizontal stabilizers 1222 and a vertical stabilizer 1224.

The fuselage 1218 of the aircraft 1210 defines an internal cabin 1230, which includes a flight deck or cockpit, one or more work sections (for example, galleys, personnel carry-on baggage areas, and the like), one or more passenger sections (for example, first class, business class, and coach sections), one or more lavatories, and/or the like.

Embodiments of the present disclosure are used to disinfect various components within the internal cabin 1230. Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figures 43A, 43B:
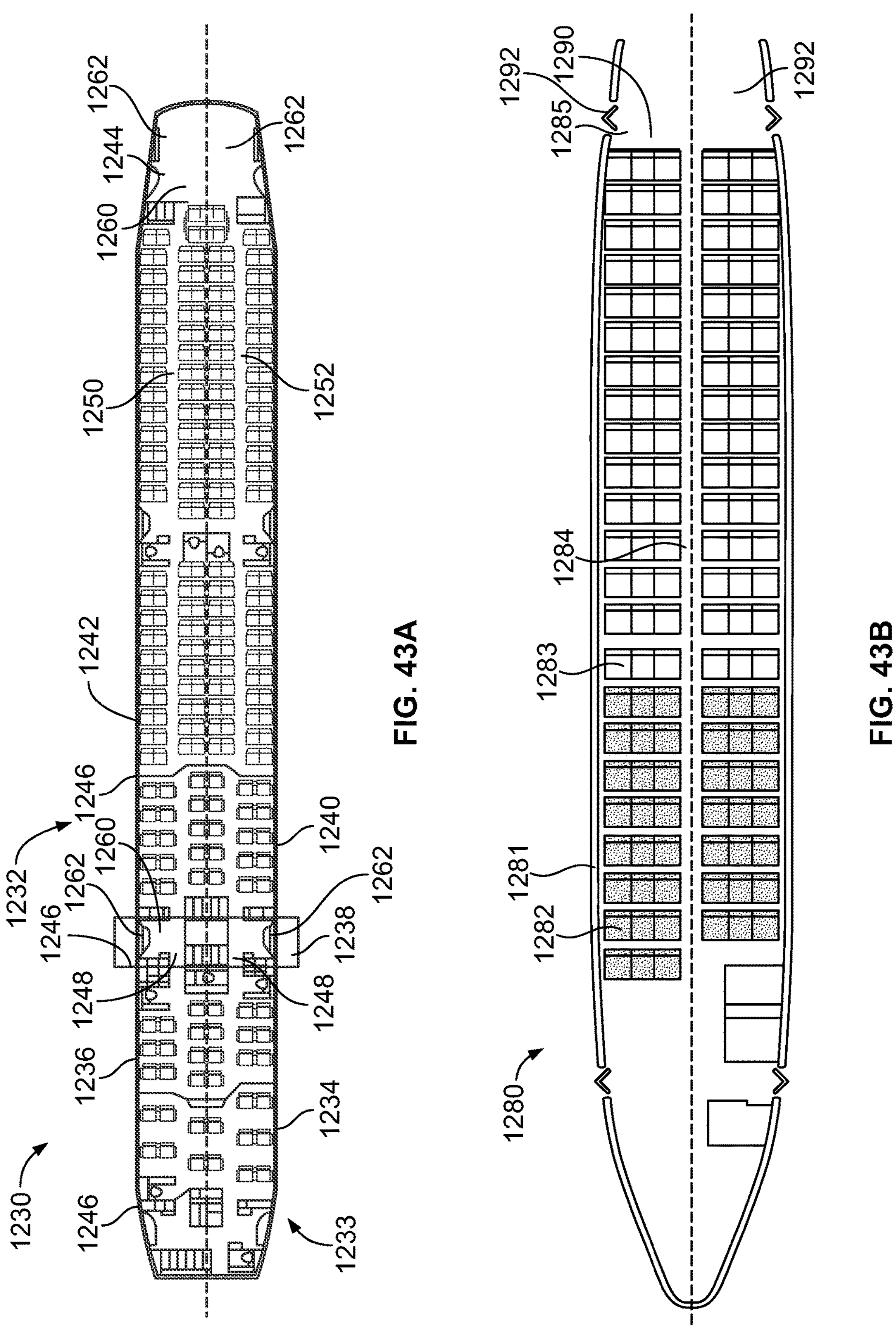
FIG. 43A illustrates a top plan view of an internal cabin of an aircraft, according to an embodiment of the present disclosure.
FIG. 43B illustrates a top plan view of an internal cabin of an aircraft, according to an embodiment of the present disclosure.

FIG. 43A illustrates a top plan view of an internal cabin 1230 of an aircraft, according to an embodiment of the present disclosure. The internal cabin 1230 may be within the fuselage 1232 of the aircraft, such as the fuselage 1218 of FIG. 42. For example, one or more fuselage walls may define the internal cabin 1230. The internal cabin 1230 includes multiple sections, including a front section 1233, a first class section 1234, a business class section 1236, a front galley station 1238, an expanded economy or coach section 1240, a standard economy of coach section 1242, and an aft section 1244, which may include multiple lavatories and galley stations. It is to be understood that the internal cabin 1230 may include more or less sections than shown. For example, the internal cabin 1230 may not include a first class section, and may include more or less galley stations than shown. Each of the sections may be separated by a cabin transition area 1246, which may include class divider assemblies between aisles 1248.

As shown in FIG. 43A, the internal cabin 1230 includes two aisles 1250 and 1252 that lead to the aft section 1244. Optionally, the internal cabin 1230 may have less or more aisles than shown. For example, the internal cabin 1230 may include a single aisle that extends through the center of the internal cabin 1230 that leads to the aft section 1244.

The aisles 1248, 1250, and 1252 extend to egress paths or door passageways 1260. Exit doors 1262 are located at ends of the egress paths 1260. The egress paths 1260 may be perpendicular to the aisles 1248, 1250, and 1252. The internal cabin 1230 may include more egress paths 1260 at different locations than shown. Embodiments of the present disclosure shown and described with respect to FIGS. 1-41 may be used to sanitize various structures within the internal cabin 1230, such as passenger seats, monuments, stowage bin assemblies, components on and within lavatories, galley equipment and components, and/or the like.

FIG. 43B illustrates a top plan view of an internal cabin 1280 of an aircraft, according to an embodiment of the present disclosure. The internal cabin 1280 is an example of the internal cabin 1230 shown in FIG. 30. The internal cabin 1280 may be within a fuselage 1281 of the aircraft. For example, one or more fuselage walls may define the internal cabin 1280. The internal cabin 1280 includes multiple sections, including a main cabin 1282 having passenger seats 1283, and an aft section 1285 behind the main cabin 1282. It is to be understood that the internal cabin 1280 may include more or less sections than shown.

The internal cabin 1280 may include a single aisle 1284 that leads to the aft section 1285. The single aisle 1284 may extend through the center of the internal cabin 1280 that leads to the aft section 1285. For example, the single aisle 1284 may be coaxially aligned with a central longitudinal plane of the internal cabin 1280.

The aisle 1284 extends to an egress path or door passageway 1290. Exit doors 1292 are located at ends of the egress path 1290. The egress path 1290 may be perpendicular to the aisle 1284. The internal cabin 1280 may include more egress paths than shown. Embodiments of the present disclosure shown and described with respect to FIGS. 1-41 may be used to sanitize various structures within the internal cabin 1230, such as passenger seats, monuments, stowage bin assemblies, components on and within lavatories, galley equipment and components, and/or the like.

Figure 44:
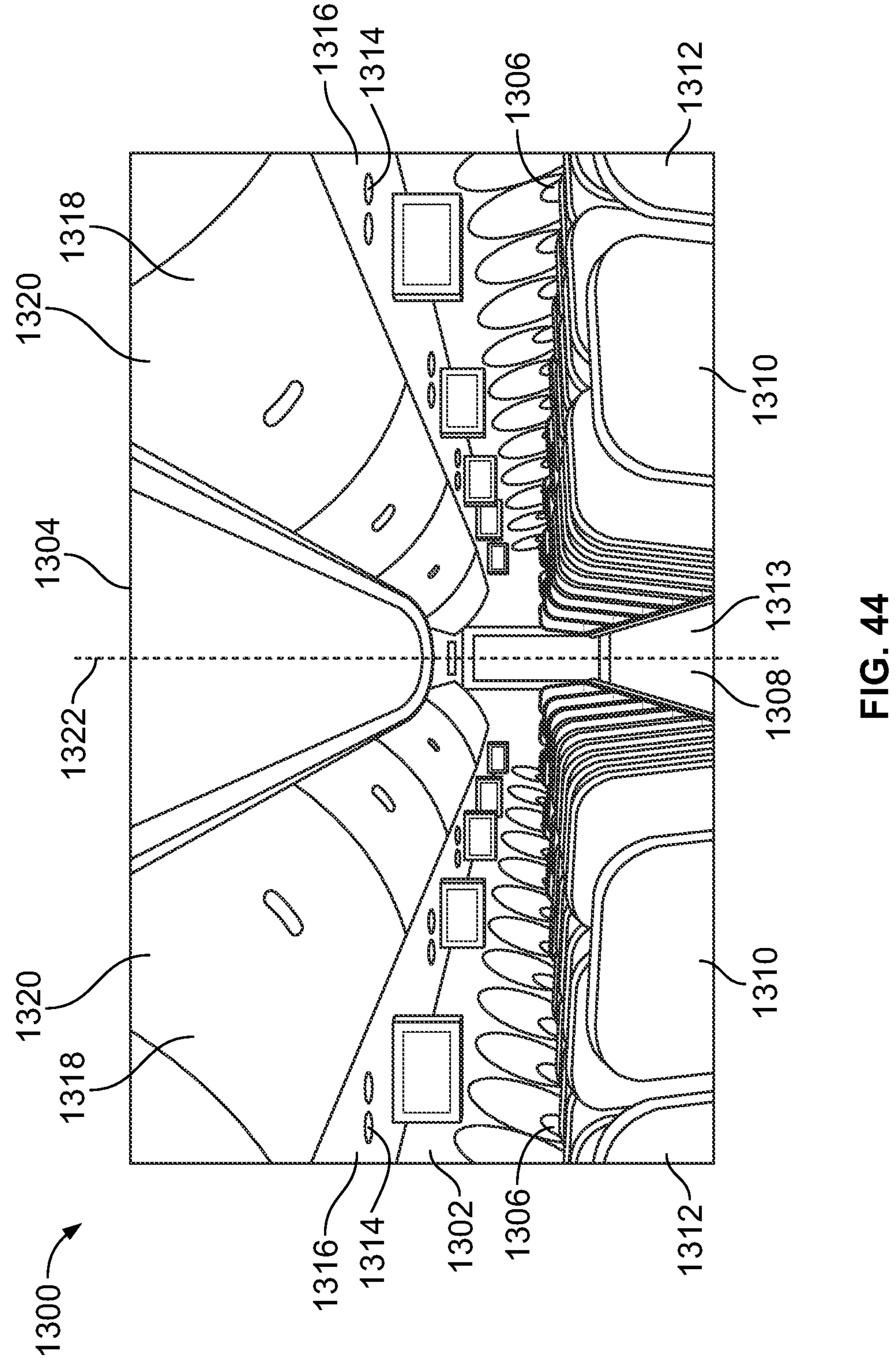
FIG. 44 illustrates a perspective interior view of an internal cabin of an aircraft, according to an embodiment of the present disclosure.

FIG. 44 illustrates a perspective interior view of an internal cabin 1300 of an aircraft, according to an embodiment of the present disclosure. The internal cabin 1300 includes outboard walls 1302 connected to a ceiling 1304. Windows 1306 may be formed within the outboard walls 1302. A floor 1308 supports rows of seats 1310. As shown in FIG. 44, a row 1312 may include two seats 1310 on either side of an aisle 1313. However, the row 1312 may include more or less seats 1310 than shown. Additionally, the internal cabin 1300 may include more aisles than shown.

Passenger service units (PSUs) 1314 are secured between an outboard wall 1302 and the ceiling 1304 on either side of the aisle 1313. The PSUs 1314 extend between a front end and rear end of the internal cabin 1300. For example, a PSU 1314 may be positioned over each seat 1310 within a row 1312. Each PSU 1314 may include a housing 1316 that generally contains vents, reading lights, an oxygen bag drop panel, an attendant request button, and other such controls over each seat 1310 (or groups of seats) within a row 1312.

Overhead stowage bin assemblies 1318 are secured to the ceiling 1304 and/or the outboard wall 1302 above and inboard from the PSU 1314 on either side of the aisle 1313. The overhead stowage bin assemblies 1318 are secured over the seats 1310. The overhead stowage bin assemblies 1318 extend between the front and rear end of the internal cabin 1300. Each stowage bin assembly 1318 may include a pivot bin or bucket 1320 pivotally secured to a strongback (hidden from view in FIG. 44). The overhead stowage bin assemblies 1318 may be positioned above and inboard from lower surfaces of the PSUs 1314. The overhead stowage bin assemblies 1318 are configured to be pivoted open in order to receive passenger carry-on baggage and personal items, for example.

As used herein, the term "outboard" means a position that is further away from a central longitudinal plane 1322 of the internal cabin 1300 as compared to another component. The term "inboard" means a position that is closer to the central longitudinal plane 1322 of the internal cabin 1300 as compared to another component. For example, a lower surface of a PSU 1314 may be outboard in relation to a stowage bin assembly 1318.

Embodiments of the present disclosure shown and described with respect to FIGS. 1-41 may be used to sanitize various structures shown within the internal cabin 1300.

As described herein, certain embodiments of the present disclosure provide systems and methods that allow for efficient production and maintenance of a UV lamp. Further, certain embodiments of the present disclosure provide systems and methods that ensures that UV light disinfection of one or more components within an area occurs when the area is unoccupied. Also, certain embodiments of the present disclosure provide systems and methods reduce EMI emanating from UV light emitters.

Additionally, embodiments of the present disclosure provide UV disinfection systems that can be easily mounted and secured throughout an area, such as internal cabin of an aircraft.

Further, the disclosure comprises embodiments according to the following clauses:

Clause 1. A system for disinfecting one or more components, the system comprising:

- one or more ultraviolet (UV) lamps, wherein the one or more UV lamps comprises:
- one or more UV light emitters configured to emit UV light; and
- a mounting interface removably securable to a securing mount.

Clause 2. The system of Clause 1, further comprising a control unit configured to control operation of the one or more UV light emitters.

Clause 3. The system of Clause 2, wherein the one or more UV lamps comprises the control unit.

Clause 4. The system of Clauses 1 or 2, wherein the one or more UV lamps comprises one or more sensors in communication with the control unit, wherein the one or more sensors are configured to detect presence or movement proximate to the one or more UV lamps.

Clause 5. The system of Clause 4, wherein the control unit is configured to control one or more of a power level, an irradiance level, an intensity level, or a timing period for disinfection of the one or more UV lamps based on presence signals received from the one or more sensors.

Clause 6. The system of Clauses 4 or 5, wherein the control unit is configured to predict future operation of the one or more UV light emitters based on presence data stored in a memory.

Clause 7. The system of any of Clauses 2-6, wherein the one or more UV lamps comprises a position detector in communication with the control unit, wherein the position detector is configured to detect a location of the one or more UV lamps within an area.

Clause 8. The system of Clause 7, wherein the control unit is configured to operate the one or more UV light emitters based on the location of the UV lamp, as detected by the position detector, within the area.

Clause 9. The system of any of Clauses 1-8, wherein the one or more UV light emitters comprise:

- first UV light emitters configured to emit the UV light at a first wavelength; and
- second UV light emitters configured to emit the UV light at a second wavelength that differs from the first wavelength.

Clause 10. The system of any of Clauses 1-9, wherein the control unit is configured to control the one or more UV light emitters to emit the UV light at different wavelengths based on sensed or predicted behavior proximate to the UV lamp.

Clause 11. The system of any of Clauses 1-10, wherein the one or more UV lamps comprises:

- a power supply; and
- one or more batteries.

Clause 12. The system of any of Clauses 1-11, wherein the control unit is configured to operate the one or more UV light emitters based on a sensed output voltage.

Clause 13. The system of any of Clauses 1-12, wherein the one or more UV lamps comprise a plurality of UV lamps, wherein the plurality of UV lamps are configured to communicate with each other.

Clause 14. The system of any of Clauses 1-13, further comprising an external monitoring system in communication with the one or more UV lamps, wherein the external monitoring system is configured to control the one or more UV lamps.

Clause 15. A method for disinfecting one or more components, the method comprising:

- removably securing one or more ultraviolet (UV) lamps including one or more UV light emitters configured to emit UV light to a securing mount.

Clause 16. The method of Clause 15, further comprises controlling, by a control unit, operation of the one or more UV light emitters.

Clause 17. The method of Clause 16, further comprising disposing the control within the one or more UV lamps.

Clause 18. The method of any of Clauses 15-17, further comprising:

- communicatively coupling one or more sensors of the one or more UV lamps with the control unit; and
- detecting, by the one or more sensors, presence or movement proximate to the one or more UV lamps.

Clause 19. The method of Clause 18, further comprising controlling, by the control unit, one or more of a power level, an irradiance level, an intensity level, or a timing period for disinfection of the one or more UV lamps based on presence signals received from the one or more sensors.

Clause 20. The method of Clauses 18 or 19, further comprising predicting, by the control unit, future operation of the one or more UV light emitters based on presence data stored in a memory.

Clause 21. The method of any of Clauses 16-20, further comprising:

- communicatively coupling a position detector of the one or more UV lamps with the control unit; and
- detecting, by the position detector, a location of the one or more UV lamps within an area.

Clause 22. The method of Clause 21, further comprising operating, by the control unit, the one or more UV light emitters based on the location of the UV lamp, as detected by the position detector, within the area.

Clause 23. The method of any of Clauses 15-22, further comprising:

emitting, by first UV light emitters, the UV light at a first wavelength; and emitting, by second UV light emitters, the UV light at a second wavelength that differs from the first wavelength.

Clause 24. The method of any of Clauses 15-23, further comprising controlling, by the control unit, the one or more UV light emitters to emit the UV light at different wavelengths based on sensed or predicted behavior proximate to the UV lamp.

Clause 25. The method of any of Clauses 15-24, further comprising providing the one or more UV lamps with a power supply, and one or more batteries.

Clause 26. The method of any of Clauses 15-25, further comprising operating, by the control unit, the one or more UV light emitters based on a sensed output voltage.

Clause 27. The method of any of Clauses 15-26, wherein the one or more UV lamps comprise a plurality of UV lamps, wherein the method further comprises communicating between the plurality of UV lamps.

Clause 28. The method of any of Clauses 15-27, further comprising:

communicatively coupling an external monitoring system with the one or more UV lamps; and controlling, by the external monitoring system, the one or more UV lamps.

Clause 29. A system for disinfecting one or more components, the system comprising:

a first subset of one or more ultraviolet (UV) lamps secured within a first area;

a second subset of one or more UV lamps secured within a second area that is spaced apart from the first area, wherein each UV lamp in the first subset and the second subset comprises:

one or more UV light emitters configured to emit UV light, and a mounting interface removably securable to a respective securing mount; and a control unit configured to control operation of the one or more UV light emitters in each of the UV lamps in the first subset and the second subset.

Clause 30. The system of Clause 29, wherein the first and second areas are both within an internal cabin of a vehicle.

Clause 31. The system of Clause 30, wherein the vehicle is a commercial aircraft.

Clause 32. The system of any of Clauses 29-31, wherein each of the first subset of the one or more UV lamps and the second subset of the one or more UV lamps comprises one or more sensors in communication with the control unit, wherein the one or more sensors of the first subset are configured to detect presence or movement proximate to the first area and the one or more sensors of the second subset are configured to detect presence or movement proximate to the second area.

Clause 33. The system of Clause 32, wherein the control unit is configured to control operation of the one or more UV light emitters in the first subset based on signals received from the one or more sensors of the first subset, and the control unit is configured to control operation of the one or more UV light emitters in the second subset based on signals received from the one or more sensors of the second subset.

Clause 34. The system of any of Clauses 29-33, wherein the control unit is configured to control the one or more UV light emitters in the first subset to emit the UV light at different wavelengths based on sensed or predicted behavior proximate to the first subset of the one or more UV lamps, and is configured to control the one or more UV light emitters in the second subset to emit the UV light at different wavelengths based on sensed or predicted behavior proximate to the second subset of the one or more UV lamps.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system for disinfecting one or more components, the system comprising:

an ultraviolet (UV) lamp, wherein the UV lamp comprises:

a housing;

one or more UV light emitters retained by the housing, the one or more UV light emitters configured to emit UV light;

a communication device retained by the housing;

one or more sensors retained by the housing;

a position detector retained by the housing;

a memory retained by the housing;

a control unit retained by the housing, wherein the control unit is in communication with the one or more UV light emitters, the communication device, the one or more sensors, the position detector, and the memory, wherein the control unit is configured to control operation of the one or more UV light emitters; and a mounting interface on or within the housing, the mounting interface removably securable to a securing mount.

2. The system of claim 1, wherein the one or more sensors are configured to detect presence or movement proximate to the UV lamp.

3. The system of claim 1, wherein the control unit is further configured to control a power level, an irradiance level, an intensity level, and a timing period for disinfection of the UV lamp based on presence signals received from the one or more sensors.

4. The system of claim 1, wherein the control unit is further configured to predict future operation of the one or more UV light emitters based on presence data stored in the memory.

5. The system of claim 1, wherein the position detector is configured to detect a location of the UV lamp within an area.

6. The system of claim 5, wherein the control unit is further configured to operate the one or more UV light emitters based on the location of the UV lamp, as detected by the position detector, within the area.

7. The system of claim 1, wherein the one or more UV light emitters comprise:

first UV light emitters configured to emit the UV light at a first wavelength; and second UV light emitters configured to emit the UV light at a second wavelength that differs from the first wavelength.

8. The system of claim 1, wherein the control unit is further configured to control the one or more UV light emitters to emit the UV light at different wavelengths based on sensed and predicted behavior proximate to the UV lamp.

9. The system of claim 1, wherein the UV lamp further comprises:

a power supply retained by the housing; and one or more batteries retained by the housing.

10. The system of claim 1, wherein the control unit is further configured to operate the one or more UV light emitters based on a sensed output voltage.

11. The system of claim 1, wherein the communication device is configured to communicate data with one or more other UV lamps.

12. The system of claim 1, further comprising an external monitoring system in communication with the UV lamp, wherein the external monitoring system is configured to control the UV lamp.

13. The system of claim 1, wherein the mounting interface comprises a plug, and the securing mounting comprises a reciprocal socket, wherein the plug is configured to be plugged into the reciprocal socket.

14. The system of claim 1, wherein the control unit is further configured to:

analyze mapping data stored in the memory, apply logical or physical mapping to determine an environment of the UV lamp, and determine disinfection requirements based on the environment.

15. A method for a system for disinfecting one or more components, the system comprising:

an ultraviolet (UV) lamp, wherein the UV lamp comprises:

a housing;

one or more UV light emitters retained by the housing, the one or more UV light emitters configured to emit UV light;

a communication device retained by the housing;

one or more sensors retained by the housing;

a position detector retained by the housing;

a memory retained by the housing;

a control unit retained by the housing, wherein the control unit is in communication with the one or more UV light emitters, the communication device, the one or more sensors, the position detector, and the memory, wherein the control unit is configured to control operation of the one or more UV light emitters; and a mounting interface on or within the housing, the mounting interface removably securable to a securing mount, the method comprising removably securing the UV lamp to the securing mount.

16. The method of claim 15, further comprises controlling, by the control unit, operation of the one or more UV light emitters.

17. The method of claim 15, further comprising-detecting, by the one or more sensors, presence or movement proximate to the UV lamp.

18. The method of claim 15, further comprising controlling, by the control unit, a power level, an irradiance level, an intensity level, and a timing period for disinfection of the UV lamp based on presence signals received from the one or more sensors.

19. The method of claim 15, further comprising predicting, by the control unit, future operation of the one or more UV light emitters based on presence data stored in the memory.

20. The method of claim 15, further comprising detecting, by the position detector, a location of the UV lamp within an area.

21. The method of claim 20, further comprising operating, by the control unit, the one or more UV light emitters based on the location of the UV lamp, as detected by the position detector, within the area.

22. The method of claim 15, further comprising:

emitting, by first UV light emitters, the UV light at a first wavelength; and emitting, by second UV light emitters, the UV light at a second wavelength that differs from the first wavelength.

23. The method of claim 15, further comprising controlling, by the control unit, the one or more UV light emitters to emit the UV light at different wavelengths based on sensed or predicted behavior proximate to the UV lamp.

24. The method of claim 15, further comprising providing the UV lamp with a power supply, and one or more batteries.

25. The method of claim 15, further comprising operating, by the control unit, the one or more UV light emitters based on a sensed output voltage.

26. The method of claim 15, further comprising communicating data, via the communication device, with one or more other UV lamps.

27. The method of claim 15, further comprising:

communicatively coupling an external monitoring system with the UV lamp; and controlling, by the external monitoring system, the UV lamp.

28. A system for disinfecting one or more components, the system comprising:

a first subset of one or more ultraviolet (UV) lamps secured within a first area;

a second subset of one or more UV lamps secured within a second area that is spaced apart from the first area, wherein each UV lamp in the first subset and the second subset comprises:

a housing;

one or more UV light emitters retained by the housing, the one or more UV light emitters configured to emit UV light;

a communication device retained by the housing;

one or more sensors retained by the housing;

a position detector retained by the housing;

a memory retained by the housing;

a first control unit retained by the housing, wherein the first control unit is in communication with the one or more UV light emitters, the communication device, the one or more sensors, the position detector, and the memory; and a mounting interface on or within the housing, the mounting interface removably securable to a respective securing mount; and a second control unit in communication with the first control unit of each of the UV lamps, the second control unit configured to control operation of the one or more UV light emitters in each of the UV lamps in the first subset and the second subset.

29. The system of claim 28, wherein the first and second areas are both within an internal cabin of a vehicle.

30. The system of claim 29, wherein the vehicle is a commercial aircraft.

31. The system of claim 28, wherein the one or more sensors of the first subset are configured to detect presence or movement proximate to the first area and the one or more sensors of the second subset are configured to detect presence or movement proximate to the second area.

32. The system of claim 31, wherein the second control unit is configured to control operation of the one or more UV light emitters in the first subset based on signals received from the one or more sensors of the first subset, and the second control unit is configured to control operation of the one or more UV light emitters in the second subset based on signals received from the one or more sensors of the second subset.

33. The system of claim 28, wherein the second control unit is configured to control the one or more UV light emitters in the first subset to emit the UV light at different wavelengths based on sensed and predicted behavior proximate to the first subset of the one or more UV lamps, and is configured to control the one or more UV light emitters in the second subset to emit the UV light at different wavelengths based on sensed and predicted behavior proximate to the second subset of the one or more UV lamps.

34. The system of claim 28, wherein the second control unit is further configured to:

analyze mapping data stored in the memory of each of the UV lamps, apply logical or physical mapping to determine an environment of each of the UV lamps, and determine disinfection requirements for each of the UV lamps based on the environment.

* * * * *